United States Patent
King et al.

(10) Patent No.: US 10,738,117 B2
(45) Date of Patent: *Aug. 11, 2020

(54) ANTIBODIES DIRECTED AGAINST PROGRAMMED DEATH-1 (PD-1)

(71) Applicant: AnaptysBio, Inc., San Diego, CA (US)

(72) Inventors: David J. King, Encinitas, CA (US); Marilyn Kehry, San Diego, CA (US)

(73) Assignee: ANAPTYSBIO, INC., San Diego, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 15/726,287

(22) Filed: Oct. 5, 2017

(65) Prior Publication Data

US 2018/0051082 A1    Feb. 22, 2018

Related U.S. Application Data

(62) Division of application No. 14/888,557, filed as application No. PCT/US2014/036525 on May 2, 2014, now Pat. No. 9,815,897.

(60) Provisional application No. 61/818,755, filed on May 2, 2013.

(51) Int. Cl.
   *C07K 16/28* (2006.01)
   *A61K 39/395* (2006.01)
   *A61K 39/00* (2006.01)

(52) U.S. Cl.
   CPC ...... *C07K 16/2803* (2013.01); *A61K 39/3955* (2013.01); *C07K 16/28* (2013.01); *C07K 16/2818* (2013.01); *A61K 2039/507* (2013.01); *C07K 2317/24* (2013.01); *C07K 2317/33* (2013.01); *C07K 2317/565* (2013.01); *C07K 2317/76* (2013.01); *C07K 2317/92* (2013.01); *C07K 2317/94* (2013.01); *Y02A 50/386* (2018.01)

(58) Field of Classification Search
   CPC ............... C07K 16/28; C07K 16/2803; C07K 16/2896; A61K 39/3955; A61K 39/39558
   See application file for complete search history.

(56) References Cited

U.S. PATENT DOCUMENTS

| | | | |
|---|---|---|---|
| 5,122,464 A | 6/1992 | Wilson et al. | |
| 5,464,758 A | 11/1995 | Gossen et al. | |
| 5,770,359 A | 6/1998 | Wilson et al. | |
| 5,814,618 A | 9/1998 | Bujard et al. | |
| 7,029,674 B2 | 4/2006 | Carreno et al. | |
| 7,101,550 B2 | 9/2006 | Wood et al. | |
| 7,105,328 B2 | 9/2006 | Wood | |
| 7,414,171 B2 | 8/2008 | Honjo | |
| 7,488,802 B2 | 2/2009 | Collins et al. | |
| 7,595,048 B2 | 9/2009 | Honjo et al. | |
| 7,700,301 B2 | 4/2010 | Wood et al. | |
| 7,709,214 B2 | 5/2010 | Freeman et al. | |
| 8,008,449 B2 | 8/2011 | Korman et al. | |
| 8,088,905 B2 | 1/2012 | Collins et al. | |
| 8,168,757 B2 | 5/2012 | Finnefrock et al. | |
| 8,216,996 B2 | 7/2012 | Minato | |
| 8,460,886 B2 | 6/2013 | Shibayama | |
| 8,563,314 B2 | 10/2013 | Gregory | |
| 8,586,038 B2 | 11/2013 | Yang | |
| 8,609,625 B2 | 12/2013 | Lan | |
| 8,728,474 B2 | 5/2014 | Honjo et al. | |
| 8,927,697 B2 | 1/2015 | Davis et al. | |
| 8,993,731 B2 | 3/2015 | Tyson et al. | |
| 9,102,728 B2 | 8/2015 | Tyson | |
| 9,181,342 B2 | 11/2015 | Davis | |
| 9,815,897 B2* | 11/2017 | King | C07K 16/28 |
| 2002/0100068 A1 | 7/2002 | Chambon et al. | |
| 2002/0164600 A1 | 11/2002 | Freeman | |
| 2004/0213795 A1 | 10/2004 | Collins et al. | |
| 2004/0241745 A1 | 12/2004 | Honjo | |
| 2007/0041982 A1 | 2/2007 | Ponath et al. | |
| 2007/0092504 A1 | 4/2007 | Carreno | |
| 2008/0311117 A1 | 12/2008 | Collins | |
| 2009/0028857 A1 | 1/2009 | Li | |
| 2009/0093024 A1 | 4/2009 | Bowers et al. | |
| 2010/0028330 A1 | 2/2010 | Collins et al. | |
| 2010/0086550 A1 | 4/2010 | Kang | |
| 2010/0151492 A1 | 6/2010 | Ahmed | |
| 2011/0008369 A1 | 1/2011 | Finnefrock et al. | |

(Continued)

FOREIGN PATENT DOCUMENTS

| | | |
|---|---|---|
| EP | 2397155 A1 | 12/2011 |
| EP | 2638061 A1 | 9/2013 |
| WO | WO 92/08796 A1 | 5/1992 |
| WO | WO 94/28143 A1 | 12/1994 |

(Continued)

OTHER PUBLICATIONS

Acierto et al., "Biomarkers for Immunostimulatory Monoclonal Antibodies in Combination Strategies for Melanoma and Other Tumor Types," *Clinical Cancer Research*, 19(5): 1009-1020 (Mar. 1, 2013).

(Continued)

*Primary Examiner* — Jessica H Roark

(74) *Attorney, Agent, or Firm* — Fish & Richardson P.C.

(57) ABSTRACT

The invention relates to an isolated immunoglobulin heavy chain polypeptide and an isolated immunoglobulin light chain polypeptide that bind to a programmed death-1 (PD-1) protein. The invention provides a PD-1-binding agent that comprises the aforementioned immunoglobulin heavy chain polypeptide and immunoglobulin light chain polypeptide. The invention also provides related vectors, compositions, and methods of using the PD-1-binding agent to treat a cancer or an infectious disease.

9 Claims, 3 Drawing Sheets

Specification includes a Sequence Listing.

(56) References Cited

U.S. PATENT DOCUMENTS

| | | |
|---|---|---|
| 2011/0081341 A1 | 4/2011 | Honjo |
| 2011/0150892 A1 | 6/2011 | Thudium et al. |
| 2011/0171215 A1 | 7/2011 | Davis et al. |
| 2011/0171220 A1 | 7/2011 | Davis |
| 2011/0229461 A1 | 9/2011 | Tyson |
| 2011/0287485 A1 | 11/2011 | Bowers et al. |
| 2012/0039906 A1 | 2/2012 | Olive |
| 2012/0114649 A1 | 5/2012 | Langermann |
| 2012/0269806 A1 | 10/2012 | Sykes et al. |
| 2013/0035472 A1 | 2/2013 | Horlick et al. |
| 2013/0095098 A1 | 4/2013 | Tyson |
| 2013/0109843 A1 | 5/2013 | Carven |
| 2013/0133091 A1 | 5/2013 | Korman |
| 2013/0156774 A1 | 6/2013 | Kuchroo |
| 2013/0164294 A1 | 6/2013 | Honjo |
| 2013/0202623 A1 | 8/2013 | Chomont |
| 2013/0217656 A1 | 8/2013 | Tsokos |
| 2013/0291136 A1 | 10/2013 | Freeman |
| 2013/0309250 A1 | 11/2013 | Cogswell |
| 2013/0310266 A1 | 11/2013 | Liang |
| 2014/0004081 A1 | 1/2014 | Cobbold |
| 2014/0220021 A1 | 8/2014 | Shibayama et al. |
| 2015/0125955 A1 | 5/2015 | Chomont et al. |
| 2015/0152180 A1 | 6/2015 | Davis et al. |
| 2015/0203579 A1 | 7/2015 | Papadopoulos et al. |
| 2015/0210769 A1 | 7/2015 | Freeman et al. |
| 2015/0274844 A1 | 10/2015 | Blankenship et al. |
| 2015/0366174 A1 | 12/2015 | Burova et al. |
| 2016/0068586 A1 | 3/2016 | Tyson |
| 2016/0176962 A1 | 6/2016 | Murriel |
| 2016/0206754 A1 | 7/2016 | Chang |
| 2016/0208021 A1 | 7/2016 | Chang |
| 2019/0256600 A1* | 8/2019 | King .................. A61K 39/3955 |

FOREIGN PATENT DOCUMENTS

| | | |
|---|---|---|
| WO | WO 2001/014557 A1 | 3/2001 |
| WO | WO 2002/078731 A1 | 10/2002 |
| WO | WO 2003/042402 A2 | 5/2003 |
| WO | WO 2004/056875 A1 | 7/2004 |
| WO | WO 2008/083174 A3 | 7/2008 |
| WO | WO 2008/156712 A1 | 12/2008 |
| WO | WO 2009/026472 A1 | 2/2009 |
| WO | WO 2010/029434 A1 | 3/2010 |
| WO | WO 2010/029435 A1 | 3/2010 |
| WO | WO 2011/090762 A1 | 7/2011 |
| WO | WO 2011/100841 A1 | 8/2011 |
| WO | WO 2011/110604 A1 | 9/2011 |
| WO | WO 2011/110621 A1 | 9/2011 |
| WO | WO 2012/017003 A1 | 2/2012 |
| WO | WO 2012/135408 A1 | 10/2012 |
| WO | WO 2013/022091 A1 | 2/2013 |
| WO | WO 2013/128194 A1 | 9/2013 |
| WO | WO 2013/169693 A1 | 11/2013 |
| WO | WO 2013/174997 A1 | 11/2013 |
| WO | WO 2013/177102 A2 | 11/2013 |
| WO | WO 2013/181452 A1 | 12/2013 |
| WO | WO 2015/112800 A1 | 7/2015 |
| WO | WO 2015/112900 A1 | 7/2015 |
| WO | WO 2015/145360 A1 | 10/2015 |
| WO | WO 2015/196051 A1 | 12/2015 |
| WO | WO 2016/020856 A2 | 2/2016 |
| WO | WO 2016/054555 A3 | 4/2016 |
| WO | WO 2016/100882 A1 | 6/2016 |
| WO | WO 2016/100924 A1 | 6/2016 |
| WO | WO 2016/106159 A1 | 6/2016 |
| WO | WO 2016/109310 A1 | 7/2016 |
| WO | WO 2016/112870 A1 | 7/2016 |

OTHER PUBLICATIONS

Almagro et al., "Humanization of antibodies," *Frontiers in Bioscience*; 13: 1619-1633 (2008).

Altschul et al., "Gapped BLAST and PSI-BLAST: a new generation of protein database search programs," *Nucleic Acids Research*, 25(17): 3389-3402 (1997).

An, *Therapeutic Monoclonal Antibodies From Bench to Clinic* (An ed.) 3-75 (John Wiley & Sons, Inc., Hoboken, NJ 2009).

Aspeslagh et al., "Rationale for anti-OX40 cancer immunotherapy," *European Journal of Cancer*, 52: 50-66 (2016).

Barber et al., "Restoring function in exhausted CD8 T cells during chronic viral infection," *Nature*, 439: 682-687 (Feb. 9, 2006).

Bertsias et al., "Genetic, Immunologic, and Immunohistochemical Analysis of the Programmed Death 1/Programmed Death Ligand 1 Pathway in Human Systemic Lupus Erythematosus," *Arthritis & Rheumatism*, 60(1): 207-218 (Jan. 2009).

Bhatia et al., "Immunobiology of Merkel cell carcinoma: implications for immunotherapy of a polyomavirus-associated cancer," *Curr. Oncol. Rep.*, 13(6): 488-497 (Dec. 2011).

Biegert et al., "Sequence context-specific profiles for homology searching," *PNAS*, 106(10): 3770-3775 (Mar. 10, 2009).

Bird et al., "Single-Chain Antigen-Binding Proteins," *Science*, 242: 423-426 (Oct. 21, 1988).

Blank et al., "PD-L1/B7H-1 Inhibits the Effector Phase of Tumor Rejection by T Cell Receptor (TCR) Transgenic CD8$^+$ T Cells," *Cancer Research*, 64: 1140-1145 (Feb. 1, 2004).

Bowers et al., "Coupling mammalian cell surface display with somatic hypermutation for the discovery and maturation of human antibodies," *PNAS*, 108(51): 20455-20460 (Dec. 20, 2011).

Brash et al., "Strontium Phosphate Transfection of Human Cells in Primary Culture: Stable Expression of the Simian Virus 40 Large-T-Antigen Gene in Primary Human Bronchial Epithelial Cells," *Molecular and Cellular Biology*, 7(5): 2031-2034 (May 1987).

Brown et al., "Blockade of Programmed Death-1 Ligands on Dendritic Cells Enhances T Cell Activation and Cytokine Production," *The Journal of Immunology*, 170: 1257-1266 (2003).

Brown et al., "Tolerance of single, but not multiple, amino acid replacements in antibody VH CDR 2: a means of minimizing B cell wastage from somatic hypermutation?" *The Journal of Immunology*, 156.9 (1996): 3285-3291.

Conese et al., "Gene Therapy Progress and Prospects: Episomally maintained self-replicating systems," *Gene Therapy*, 11: 1735-1741 (2004).

De Genst et al., "Antibody repertoire development in camelids,"*Developmental & Comparative Immunology*, 30:187-198 (2006).

De St. Groth et al., "Production of Monoclonal Antibodies: Strategy and Tactics," *Journal of Immunological Methods*, 35: 1-21 (1980).

Dong et al., "Tumor-associated B7-H1 promotes T-cell apoptosis: A potential mechanism of immune evasion," *Nature Medicine*, 8(8): 793-800 (Aug. 2002).

Durbin et al., *Biological Sequence Analysis, Probabilistic Models of Proteins and Nucleic Acids*, (Durbin et al., ed.) 1-356 (Cambridge University Press, Cambridge, UK 1998).

Flies et al., "Blockade of the B7-H1/PD-1 Pathway for Cancer Immunotherapy," *Yale Journal of Biology and Medicine*, 84: 409-421 (2011).

Freeman et al., "Engagement of the PD-1 Immunoinhibitory Receptor by a Novel B7 Family Member Leads to Negative Regulation of Lymphocyte Activation," *J. Exp. Med.* 192(7): 1027-1034 (Oct. 2, 2000).

Fuhrmann-Benzakein et al., "Inducible and irreversible control of gene expression using a single transgene," *Nucleic Acids Research*, 28(23): 1-5 (2000).

Greenwald et al., "The B7 Family Revisited," *Annu. Rev. Immunol.*, 23: 515-548 (2005).

Hamanishi et al., "Programmed cell death 1 ligand 1 and tumor-infiltrating CD8+ T lymphocytes are prognostic factors of human ovarian cancer," *PNAS*, 104(9): 3360-3365 (Feb. 27, 2007).

Hirano et al., "Blockade of B7-H1 and PD-1 by Monoclonal Antibodies Potentiates Cancer Therapeutic Immunity," *Cancer Research*, 65(3): 1089-1096 (Feb. 1, 2005).

Holliger et al., "Engineered antibody fragments and the rise of single domains," *Nature Biotechnology*, 23(9): 1126-1136 (Sep. 2005).

(56) References Cited

OTHER PUBLICATIONS

Hötzel et al., "A strategy for risk mitigation of antibodies with fast clearance," *mAbs*, 4(6): 753-760 (Nov./Dec. 2012).
Hou et al., "Humanization of an Anti-CD34 Monoclonal Antibody by Complementarity-determining Region Grafting Based on Computer-assisted Molecular Modelling," *J. Biochem.*, 144: 115-120 (2008).
Huston et al., "Protein engineering of antibody binding sites: Recovery of specific activity in an anti-digoxin single-chain Fv analogue produced in *Escherichia coli*," *PNAS USA*, 85: 5879-5883 (Aug. 1988).
Indra et al., "Temporally-controlled site-specific mutagenesis in the basal layer of the epidermis: comparison of the recombinase activity of the tamoxifen-inducible Cre-ER$^T$ and Cre-ER$^{T2}$ recombinases," *Nucleic Acids Research*, 27(22): 4324-4327 (1999).
International Bureau of WIPO, International Preliminary Report on Patentability in International Patent Application No. PCT/US2014/036525 (dated Nov. 12, 2015).
Ishida et al., "Induced expression of PD-1, a novel member of the immunoglobulin gene superfamily, upon programmed cell death," *The EMBO Journal*, 11(11): 3887-3895 (1992).
Iwai et al., "Involvement of PD-L1 on tumor cells in the escape from host immune system and tumor immunotherapy by PD-L1 blockade," *PNAS*, 99(19): 12293-12297 (Sep. 17, 2002).
Iwai et al., "PD-1 blockade inhibits hematogenous spread of poorly immunogenic tumor cells by enhanced recruitment of effector T cells," *International Immunology*, 17(2): 133-144 (2004).
Jäck et al., "Looping out and deletion mechanism for the immunoglobulin heavychain class switch," *PNAS USA*, 85: 1581-1585 (Mar. 1988).
Kasagi et al., "Anti-Programmed Cell Death 1 Antibody Reduces CD4$^+$PD-1$^+$ T Cells and Relieves the Lupus-Like Nephritis of NZB/W F1 Mice," *The Journal of Immunology*, 184: 2337-2347 (Feb. 5, 2010).
Kashmiri et al., "SDR grafting—a new approach to antibody humanization," *Methods*, 36: 25-34 (2005).
Kearney et al., "A New Mouse Myeloma Cell Line That Has Lost Immunoglobulin Expression But Permits the Construction of Antibody-Secreting Hybrid Cell Lines," *The Journal of Immunology*, 123(4): 1548-1550 (Oct. 1979).
Kent et al., "Ouabain Resistance Conferred by Expression of the cDNA for a Murine Na$^+$,K$^+$-ATPase α Subunit," *Science*, 237: 901-903 (Aug. 21, 1987).
Kroner et al., "A PD-1 Polymorphism Is Associated with Disease Progression in Multiple Sclerosis," *Annals of Neurology*, 58(1): 50-57 (Jul. 2005).
Latchman et al., "PD-L2 is a second ligand for PD-1 and inhibits T cell activation," *Nature Immunology*, 2(3): 261-268 (Mar. 2001).
Lonberg, "Human antibodies from transgenic animals," *Nature Biotechnology*, 23(9): 1117-1125 (Sep. 2005).
Lonberg, "Human Monoclonal Antibodies from Transgenic Mice," *Therapeutic Antibodies. Handbook of Experimental Pharmacology 181*, (Chernajovsky et al., eds.), 69-97 (Springer-Verlag, Berlin 2008).
Lowy et al., "Isolation of Transforming DNA: Cloning the Hamster aprt Gene," *Cell*, 22: 817-823 (Dec. 1980).
Luckow et al., "Efficient Generation of Infectious Recombinant Baculoviruses by Site-Specific Transposon-Mediated Insertion of Foreign Genes into a Baculovirus Genome Propagated in *Escherichia coli*," *Journal of Virology*, 67(8): 4566-4579 (Aug. 1993).
Mahoney et al., "The Next Immune-Checkpoint Inhibitors: PD-1/PD-L1 Blockade in Melanoma," *Clinical Therapeutics*, 37(4):764-782 (2015).
McConnell et al., "An integrated approach to extreme thermostabilization and affinity maturation of an antibody," *Protein Engineering, Design & Selection*, 26(2): 151-163 (2013).
Mulligan et al., "Selection for animal cells that express the *Escherichia coli* gene coding for xanthine-guanine phosphoribosyltransferase," *PNAS USA*, 78(4): 2072-2076 (Apr. 1981).

Ngiow et al., "Anti-TIM3 Antibody Promotes T Cell IFN-$\gamma$-Mediated Antitumor Immunity and Suppresses Established Tumors," *Cancer Res.*, 71(10): 3540-3551 (May 15, 2011).
Ni et al., "PD-1 gene haplotype is associated with the development of type 1 diabetes mellitus in Japanese children," *Hum. Genet.*, 121: 223-232 (2007).
Nielsen et al., "Association of a putative regulatory polymorphism in the PD-1 gene with susceptibility to type 1 diabetes," *Tissue Antigens*, 62: 492-497 (2003).
Nishimura et al., "Development of Lupus-like Autoimmune Diseases by Disruption of the PD-1 Gene Encoding an ITIM Motif-Carrying Immunoreceptor," *Immunity*, 11: 141-151 (Aug. 1999).
No et al., "Ecdysone-inducible gene expression in mammalian cells and transgenic mice," *PNAS USA*, 93: 3346-3351 (Apr. 1996).
Nygren, "Conjugation of Horseradish Peroxidase to Fab Fragments with Different Homobifunctional and Heterobifunctional Cross-Linking Reagents," t*The Journal of Histochemistry and Cytochemistry*, 30(5): 407-412 (1982).
O'Hare et al., "Transformation of mouse fibroblasts to methotrexate resistance by a recombinant plasmid expressing a prokaryotic dihydrofolate reductase," *PNAS USA*, 78(3): 1527-1531 (Mar. 1981).
Osbourn et al., "Directed selection of MIP-1α neutralizing CCR5 antibodies from a phage display human antibody library," *Nature Biotechnology*, 16: 778-781 (Aug. 1998).
Parry et al., "CTLA-4 and PD-1 Receptors Inhibit T-Cell Activation by Distinct Mechanisms," *Molecular and Cellular Biology*, 25(21): 9543-9553 (Nov. 2005).
Patnaik et al., "Phase I study of MK-3475 (anti-PD-1 monoclonal antibody) in patients with advanced solid tumors," *J. Clin. Oncol.*, 30(Abstract No. 2512): 30 (2012).
Porichis et al., "Role of PD-1 in HIV Pathogenesis and as Target for Therapy," *Curr. HIV/AIDS Rep.*, 9(1): 81-90 (Mar. 2012).
Sanmamed et al., "Agonists of Co-stimulation in Cancer Immunotherapy Directed Against CD137, OX40, GITR, CD27, CD28, and ICOS," *Seminars in Oncology* 42(4): 640-655 (Aug. 2015).
Sakuishi et al., "Targeting Tim-3 and PD-1 pathways to reverse T cell exhaustion and restore anti-tumor immunity," *The Journal of Experimental Medicine*, 207(10): 2187-2194 (Sep. 27, 2010).
Sharpe et al., "The function of programmed cell death 1 and its ligands in regulating autoimmunity and infection," 9*Nature Immunology*, 8(3): 239-245 (Mar. 2007).
Söding, "Protein homology detection by HMM-HMM comparison," *Bioinformatics*, 21(7): 951-960 (2005).
Szybalska et al., "Genetics of Human Cell Lines, IV. DNA-Mediated Heritable Transformation of a Biochemical Trait," *PNAS.*, 48: 2026-2034 (1962).
Tahoori et al., "Association of programmed cell death-1 (PDCD-1) gene polymorphisms with rheumatoid arthritis in Iranian patients," *Clinical and Experimental Rheumatology*, 29: 763-767 (Sep. 2011).
Tang et al., "Programmed Death 1 Pathway inhibition in Metastatic Renal Cell Cancer and Prostate Cancer," *Curr. Oncol., Rep.*, 15: 98-104 (2013).
Topalian et al., "Safety, Activity, and Immune Correlates of Anti-PD-1 Antibody in Cancer," *The New England Journal of Medicine*, 366(26): 2443-2454 (Jun. 28, 2012).
Turnis et al., "Combinatorial immunotherapy: PD-1 may not be LAG-ing behind any more." *Oncoimmunology*, 1.7 (2012): 1172-1174.
United States Patent and Trademark Office, International Search Report in International Patent Application No. PCT/US2014/036525 (dated Dec. 24, 2014).
Urlaub et al., "Isolation of Chinese hamster cell mutants deficient in dihydrofolate reductase activity," *PNAS USA*, 77(7): 4216-4220 (Jul. 1980).
Vitetta et al., "Considering Therapeutic Antibodies," *Science*, 313: 308-309 (Jul. 21, 2006).
Weber, "Immune Checkpoint Proteins: A New Therapeutic Paradigm for Cancer—Preclinical Background: CTLA-4 and PD-1 Blockade," *Seminars in Oncology*, 37(5): 430-439 (Oct. 2010).
Wigler et al., "Transfer of Purified Herpes Virus Thymidine Kinase Gene to Cultured Mouse Cells," *Cell*, 11: 223-232 (May 1977).

(56) References Cited

OTHER PUBLICATIONS

Wigler et al., "Transformation of mammalian cells with an amplifiable dominant-acting gene," *PNAS USA*, 77(6): 3567-3570 (Jun. 1980).

Woo et al., "Immune inhibitory molecules LAG-3 and PD-1 synergistically regulate T cell function to promote tumoral immune escape," *Cancer Res.*, 72(4): 917-927 (Feb. 15, 2012).

Yamazaki et al., "Expression of Programmed Death 1 Ligands by Murine T Cells and APC," *The Journal of Immunology*, 169: 5538-5545 (2002).

Search Report issued by the European Patent Office dated Oct. 28, 2016.

Extended Search Report issued by the European Patent Office for Application No. 14791454.3 dated Feb. 28, 2017.

\* cited by examiner

SEQUENCE LISTING

```
<160> NUMBER OF SEQ ID NOS: 64

<210> SEQ ID NO 1
<211> LENGTH: 10
<212> TYPE: PRT
<213> ORGANISM: Artificial Sequence
<220> FEATURE:
<223> OTHER INFORMATION: Synthetic sequence

<400> SEQUENCE: 1

Gly Phe Thr Phe Ser Ser Tyr Thr Leu Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic sequence

<400> SEQUENCE: 2

Val Ile Ser Ser Gly Gly Asp Tyr Ala Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic sequence

<400> SEQUENCE: 3
```

```
Asp His Tyr Gly Thr Ser His Phe Ala Tyr
1               5                   10
```

<210> SEQ ID NO 4
<211> LENGTH: 120
<212> TYPE: PRT
<213> ORGANISM: Artificial Sequence
<220> FEATURE:
<223> OTHER INFORMATION: synthetic sequence

<400> SEQUENCE: 4

```
Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Thr Leu Ser Trp Val Arg Gln Thr Pro Gly Lys Arg Leu Glu Trp Val
            35                  40                  45

Ala Val Ile Ser Ser Gly Gly Asp Tyr Ala Tyr Tyr Pro Asp Ser Val
        50                  55                  60

Gln Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Ser Arg Asp His Tyr Gly Thr Ser His Phe Ala Tyr Trp Gly Gln Gly
            100                 105                 110

Thr Leu Val Thr Val Ser Ala Ala
        115                 120
```

<210> SEQ ID NO 5
<211> LENGTH: 120
<212> TYPE: PRT
<213> ORGANISM: Artificial Sequence
<220> FEATURE:
<223> OTHER INFORMATION: synthetic sequence

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Thr Leu Ser Trp Val Arg Gln Ala Pro Gly Lys Gly Leu Glu Trp Val
            35                  40                  45

Ser Val Ile Ser Ser Gly Gly Asp Tyr Ala Tyr Tyr Pro Asp Ser Val
        50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Tyr Gly Thr Ser His Phe Ala Tyr Trp Gly Gln Gly
            100                 105                 110

Thr Leu Val Thr Val Ser Ser Ala
        115                 120
```

<210> SEQ ID NO 6
<211> LENGTH: 120
<212> TYPE: PRT
<213> ORGANISM: Artificial Sequence
<220> FEATURE:
<223> OTHER INFORMATION: synthetic sequence

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Val Ile Ser Ser Gly Gly Asp Ser Ala Tyr Tyr Pro Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu His Tyr Gly Thr Ser His Phe Ala Tyr Trp Gly Gln Gly
            100                 105                 110

Thr Leu Val Thr Val Ser Ser Ala
            115                 120

<210> SEQ ID NO 7
<211> LENGTH: 120
<212> TYPE: PRT
<213> ORGANISM: Artificial Sequence
<220> FEATURE:
<223> OTHER INFORMATION: synthetic sequence

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Val Ile Ser Ser Gly Gly Asn Ser Ala Tyr Tyr Pro Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu His Tyr Gly Thr Ser His Phe Ala Tyr Trp Gly Gln Gly
            100                 105                 110

Thr Leu Val Thr Val Ser Ser Ala
            115                 120

<210> SEQ ID NO 8
<211> LENGTH: 120
<212> TYPE: PRT
<213> ORGANISM: Artificial Sequence
<220> FEATURE:
<223> OTHER INFORMATION: synthetic sequence

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

```
Ser Val Ile Ser Ser Gly Gly Asn Tyr Ala Tyr Tyr Pro Asp Ser Val
            50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu His Tyr Gly Thr Ser His Phe Ala Tyr Trp Gly Gln Gly
            100                 105                 110

Thr Leu Val Thr Val Ser Ser Ala
        115                 120

<210> SEQ ID NO 9
<211> LENGTH: 120
<212> TYPE: PRT
<213> ORGANISM: Artificial Sequence
<220> FEATURE:
<223> OTHER INFORMATION: synthetic sequence

<400> SEQUENCE: 9

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Thr Met Ser Trp Val Arg Gln Ala Pro Gly Lys Gly Leu Glu Trp Val
         35                  40                  45

Ser Val Ile Ser Ser Gly Gly Asp Ser Thr Tyr Tyr Pro Asp Ser Val
            50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu His Tyr Gly Thr Ser His Phe Ala Tyr Trp Gly Gln Gly
            100                 105                 110

Thr Leu Val Thr Val Ser Ser Ala
        115                 120

<210> SEQ ID NO 10
<211> LENGTH: 120
<212> TYPE: PRT
<213> ORGANISM: Artificial Sequence
<220> FEATURE:
<223> OTHER INFORMATION: synthetic sequence

<400> SEQUENCE: 10

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Thr Met Ser Trp Val Arg Gln Ala Pro Gly Lys Gly Leu Glu Trp Val
         35                  40                  45

Ser Val Ile Ser Ser Gly Gly Asn Ser Ala Tyr Tyr Pro Asp Ser Val
            50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Tyr Tyr Gly Ser Ser His Phe Ala Tyr Trp Gly Gln Gly
```

Thr Leu Val Thr Val Ser Ser Ala
        115                 120

<210> SEQ ID NO 11
<211> LENGTH: 120
<212> TYPE: PRT
<213> ORGANISM: Artificial Sequence
<220> FEATURE:
<223> OTHER INFORMATION: synthetic sequence

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Val Ile Ser Ser Gly Gly Asn Ser Ala Tyr Tyr Pro Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu His Tyr Gly Ser Ser His Phe Ala Tyr Trp Gly Gln Gly
            100                 105                 110

Thr Leu Val Thr Val Ser Ser Ala
        115                 120

<210> SEQ ID NO 12
<211> LENGTH: 10
<212> TYPE: PRT
<213> ORGANISM: Artificial Sequence
<220> FEATURE:
<223> OTHER INFORMATION: synthetic sequence

<400> SEQUENCE: 12

Gly Phe Thr Phe Ser Ser Tyr Thr Met Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic sequence

<400> SEQUENCE: 13

Val Ile Ser Ser Gly Gly Asn Ser Thr Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetic sequence

<400> SEQUENCE: 14

Glu His Tyr Gly Ser Ser His Phe Ala Tyr
1               5                   10

<210> SEQ ID NO 15
<211> LENGTH: 120
<212> TYPE: PRT
<213> ORGANISM: Artificial Sequence
<220> FEATURE:
<223> OTHER INFORMATION: synthetic sequence

<400> SEQUENCE: 15

Asp Val Lys Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Val Ile Ser Ser Gly Gly Asn Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Glu His Tyr Gly Ser Ser His Phe Ala Tyr Trp Gly Gln Gly
            100                 105                 110

Thr Leu Val Thr Val Ser Ala Ala
        115                 120

<210> SEQ ID NO 16
<211> LENGTH: 120
<212> TYPE: PRT
<213> ORGANISM: Artificial Sequence
<220> FEATURE:
<223> OTHER INFORMATION: synthetic sequence

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Val Ile Ser Ser Gly Gly Asn Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu His Tyr Gly Ser Ser His Phe Ala Tyr Trp Gly Gln Gly
            100                 105                 110

Thr Leu Val Thr Val Ser Ser Ala
        115                 120

<210> SEQ ID NO 17
<211> LENGTH: 120
<212> TYPE: PRT
<213> ORGANISM: Artificial Sequence
<220> FEATURE:
<223> OTHER INFORMATION: synthetic sequence

<400> SEQUENCE: 17

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
        20                  25                  30

Thr Leu Ser Trp Val Arg Gln Ala Pro Gly Lys Gly Leu Glu Trp Val
            35                  40                  45

Ser Val Ile Ser Ser Gly Gly Asn Tyr Ala Tyr Tyr Pro Asp Ser Val
 50                  55                  60

Gln Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                85                  90                  95

Ala Lys Glu His Tyr Gly Thr Ser His Phe Ala Tyr Trp Gly Gln Gly
            100                 105                 110

Thr Leu Val Thr Val Ser Ser Ala
        115                 120

<210> SEQ ID NO 18
<211> LENGTH: 120
<212> TYPE: PRT
<213> ORGANISM: Artificial Sequence
<220> FEATURE:
<223> OTHER INFORMATION: synthetic sequence

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Leu Ser Trp Val Arg Gln Ala Pro Gly Lys Gly Leu Glu Trp Val
        35                  40                  45

Ser Val Ile Ser Ser Gly Gly Asn Tyr Ala Tyr Tyr Pro Asp Ser Val
 50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                85                  90                  95

Ala Lys Glu His Tyr Gly Thr Ser His Phe Ala Tyr Trp Gly Gln Gly
            100                 105                 110

Thr Leu Val Thr Val Ser Ser Ala
        115                 120

<210> SEQ ID NO 19
<211> LENGTH: 10
<212> TYPE: PRT
<213> ORGANISM: Artificial Sequence
<220> FEATURE:
<223> OTHER INFORMATION: synthetic sequence

<400> SEQUENCE: 19

Gly Phe Thr Phe Ser Ser Tyr Asp Met Ser
1               5                   10

<210> SEQ ID NO 20
<211> LENGTH: 10
<212> TYPE: PRT
<213> ORGANISM: Artificial Sequence
<220> FEATURE:
<223> OTHER INFORMATION: synthetic sequence

<400> SEQUENCE: 20
```

```
Thr Ile Ser Gly Gly Gly Ser Tyr Thr Tyr
1               5                   10
```

<210> SEQ ID NO 21
<211> LENGTH: 7
<212> TYPE: PRT
<213> ORGANISM: Artificial Sequence
<220> FEATURE:
<223> OTHER INFORMATION: synthetic sequence

<400> SEQUENCE: 21

```
Pro Tyr Tyr Ala Met Asp Tyr
1               5
```

<210> SEQ ID NO 22
<211> LENGTH: 117
<212> TYPE: PRT
<213> ORGANISM: Artificial Sequence
<220> FEATURE:
<223> OTHER INFORMATION: synthetic sequence

<400> SEQUENCE: 22

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Asp Met Ser Trp Val Arg Gln Thr Pro Glu Lys Arg Leu Glu Trp Val
            35                  40                  45

Ala Thr Ile Ser Gly Gly Gly Ser Tyr Thr Tyr Tyr Gln Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Ser Pro Tyr Tyr Ala Met Asp Tyr Trp Gly Gln Gly Thr Ser Val
            100                 105                 110

Thr Val Ser Ser Ala
            115
```

<210> SEQ ID NO 23
<211> LENGTH: 117
<212> TYPE: PRT
<213> ORGANISM: Artificial Sequence
<220> FEATURE:
<223> OTHER INFORMATION: synthetic sequence

<400> SEQUENCE: 23

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Thr Ile Ser Gly Gly Gly Ser Tyr Thr Tyr Tyr Gln Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
```

Thr Val Ser Ser Ala
        115

<210> SEQ ID NO 24
<211> LENGTH: 117
<212> TYPE: PRT
<213> ORGANISM: Artificial Sequence
<220> FEATURE:
<223> OTHER INFORMATION: synthetic sequence

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala
        115

<210> SEQ ID NO 25
<211> LENGTH: 117
<212> TYPE: PRT
<213> ORGANISM: Artificial Sequence
<220> FEATURE:
<223> OTHER INFORMATION: synthetic sequence

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Arg Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala
        115

<210> SEQ ID NO 26
<211> LENGTH: 15
<212> TYPE: PRT
<213> ORGANISM: Artificial Sequence
<220> FEATURE:

<223> OTHER INFORMATION: synthetic sequence

<400> SEQUENCE: 26

Arg Ala Ser Glu Ser Val Asp Asn Phe Gly Ile Ser Phe Met Ser
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: synthetic sequence

<400> SEQUENCE: 27

Ala Ala Ser Asn Pro Gly Ser
1               5

<210> SEQ ID NO 28
<211> LENGTH: 112
<212> TYPE: PRT
<213> ORGANISM: Artificial Sequence
<220> FEATURE:
<223> OTHER INFORMATION: synthetic sequence

<400> SEQUENCE: 28

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Phe
                20                  25                  30

Gly Ile Ser Phe Met Ser Trp Phe Gln Gln Lys Pro Gly Gln Pro Pro
            35                  40                  45

Lys Leu Leu Ile Tyr Ala Ala Ser Asn Pro Gly Ser Gly Val Pro Ala
    50                  55                  60

Arg Phe Ser Gly Ser Val Ser Gly Thr Asp Phe Ser Leu Asn Ile His
65                  70                  75                  80

Pro Met Glu Glu Asp Ala Ala Met Tyr Phe Cys Gln Gln Ser Lys
                85                  90                  95

Glu Val Pro Tyr Thr Phe Gly Gly Gly Thr Lys Leu Glu Ile Lys Arg
                100                 105                 110

<210> SEQ ID NO 29
<211> LENGTH: 112
<212> TYPE: PRT
<213> ORGANISM: Artificial Sequence
<220> FEATURE:
<223> OTHER INFORMATION: synthetic sequence

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Phe
                20                  25                  30

Gly Ile Ser Phe Met Ser Trp Tyr Gln Gln Lys Pro Gly Gln Ala Pro
            35                  40                  45

Arg Leu Leu Ile Tyr Ala Ala Ser Asn Pro Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Tyr Thr Phe Gly Gln Gly Thr Lys Leu Glu Ile Lys Arg
            100                 105                 110

<210> SEQ ID NO 30
<211> LENGTH: 15
<212> TYPE: PRT
<213> ORGANISM: Artificial Sequence
<220> FEATURE:
<223> OTHER INFORMATION: synthetic sequence

<400> SEQUENCE: 30

Arg Ala Ser Glu Ser Val Asp Lys Tyr Gly Ile Ser Phe Met Ser
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: synthetic sequence

<400> SEQUENCE: 31

Ala Ala Ser Asn Gln Gly Ser
1               5

<210> SEQ ID NO 32
<211> LENGTH: 112
<212> TYPE: PRT
<213> ORGANISM: Artificial Sequence
<220> FEATURE:
<223> OTHER INFORMATION: synthetic sequence

<400> SEQUENCE: 32

Asp Ile Val Leu Thr Gln Ser Pro Asp Ser Leu Ala Val Ser Leu Gly
1               5                   10                  15

Leu Arg Ala Thr Ile Ser Cys Arg Ala Ser Glu Ser Val Asp Lys Tyr
            20                  25                  30

Gly Ile Ser Phe Met Ser Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Tyr Thr Phe Gly Gly Gly Thr Lys Leu Glu Ile Lys Arg
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: synthetic sequence

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Lys Tyr
            20                  25                  30

Gly Ile Ser Phe Met Ser Trp Tyr Gln Gln Lys Pro Gly Gln Pro Pro
        35                  40                  45

```
Lys Leu Leu Ile Tyr Ala Ala Ser Asn Gln Gly Ser Gly Val Pro Asp
         50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Val Pro Tyr Thr Phe Gly Gln Gly Thr Lys Leu Glu Ile Lys Arg
                100                 105                 110

<210> SEQ ID NO 34
<211> LENGTH: 129
<212> TYPE: PRT
<213> ORGANISM: Artificial Sequence
<220> FEATURE:
<223> OTHER INFORMATION: synthetic sequence

<400> SEQUENCE: 34

Asp Ile Val Met Thr Gln Ser Pro Asp Ser Leu Ala Val Ser Leu Gly
 1               5                  10                  15

Glu Arg Ala Thr Ile Asn Cys Arg Ala Ser Glu Ser Val Asp Lys Tyr
                 20                  25                  30

Gly Ile Thr Phe Met Ser Trp Tyr Gln Gln Lys Pro Gly Gln Pro Pro
             35                  40                  45

Lys Leu Leu Ile Tyr Ala Ala Ser Asn Gln Gly Ser Gly Val Pro Asp
         50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Val Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu

<210> SEQ ID NO 35
<211> LENGTH: 11
<212> TYPE: PRT
<213> ORGANISM: Artificial Sequence
<220> FEATURE:
<223> OTHER INFORMATION: synthetic sequence

<400> SEQUENCE: 35

Lys Ala Ser Gln Asp Val Gly Thr Ala Val Ala
 1               5                  10

<210> SEQ ID NO 36
<211> LENGTH: 7
<212> TYPE: PRT
<213> ORGANISM: Artificial Sequence
<220> FEATURE:
<223> OTHER INFORMATION: synthetic sequence

<400> SEQUENCE: 36

Trp Ala Ser Thr Arg His Thr
 1               5

<210> SEQ ID NO 37
<211> LENGTH: 9
<212> TYPE: PRT
<213> ORGANISM: Artificial Sequence
```

```
<220> FEATURE:
<223> OTHER INFORMATION: synthetic sequence

<400> SEQUENCE: 37

Gln His Tyr Ser Ser Tyr Pro Trp Thr
1               5

<210> SEQ ID NO 38
<211> LENGTH: 108
<212> TYPE: PRT
<213> ORGANISM: Artificial Sequence
<220> FEATURE:
<223> OTHER INFORMATION: synthetic sequence

<400> SEQUENCE: 38

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln His Tyr Ser Ser Tyr Pro Trp
                85                  90                  95

Thr Phe Gly Gly Gly Thr Lys Leu Glu Ile Lys Arg
            100                 105

<210> SEQ ID NO 39
<211> LENGTH: 108
<212> TYPE: PRT
<213> ORGANISM: Artificial Sequence
<220> FEATURE:
<223> OTHER INFORMATION: synthetic sequence

<400> SEQUENCE: 39

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg
            100                 105

<210> SEQ ID NO 40
<211> LENGTH: 108
<212> TYPE: PRT
<213> ORGANISM: Artificial Sequence
<220> FEATURE:
<223> OTHER INFORMATION: synthetic sequence

<400> SEQUENCE: 40
```

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg
            100                 105

<210> SEQ ID NO 41
<211> LENGTH: 108
<212> TYPE: PRT
<213> ORGANISM: Artificial Sequence
<220> FEATURE:
<223> OTHER INFORMATION: synthetic sequence

<400> SEQUENCE: 41

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln His Tyr Asn Ser Tyr Pro Trp
                85                  90                  95

Thr Phe Gly Gln Gly Thr Lys Leu Glu Ile Lys Arg
            100                 105

<210> SEQ ID NO 42
<211> LENGTH: 362
<212> TYPE: DNA
<213> ORGANISM: Artificial Sequence
<220> FEATURE:
<223> OTHER INFORMATION: synthetic sequence

<400> SEQUENCE: 42
gacgtgaagc tggtggagtc tgggggaggc ttagtgaagc ctggagggtc cctgaaactc    60
tcctgtgcag cctctggatt cactttcagt agttataccc tgtcttgggt tcgccagact   120
ccggggaaga ggctggagtg ggtcgcagtc attagtagtg gtggtgatta cgcctactat   180
ccagacagtg tgcagggccg attcaccatc tccagagaca atgccaagaa caccctgtac   240
ctgcaaatga cagtctgaa gtctgaggac acagccatgt attactgttc aagagatcac   300
tacggtacta gtcactttgc ttactggggc caagggactc tggtcactgt ctctgcagcc   360
tc                                                                  362

<210> SEQ ID NO 43

<211> LENGTH: 362
<212> TYPE: DNA
<213> ORGANISM: Artificial Sequence
<220> FEATURE:
<223> OTHER INFORMATION: synthetic sequence

<400> SEQUENCE: 43

| gaggtgcagc tgttggagtc tgggggaggc ttggtacagc ctggggggtc cctgagactc | 60 |
| tcctgtgcag cctctggatt cactttcagt agttataccc tgtcttgggt ccgccaggct | 120 |
| ccagggaagg ggctggagtg ggtctcagtc attagtagtg gtggtgatta cgcctactat | 180 |
| ccagacagtg tgcagggccg gttcaccatc tccagagaca attccaagaa cacgctgtat | 240 |
| ctgcaaatga acagcctgag agccgaggac acggccgtat attactgtgc gaaagatcac | 300 |
| tacggtacta gtcactttgc ttactggggc caaggaaccc tggtcaccgt ctcctcagca | 360 |
| tc | 362 |

<210> SEQ ID NO 44
<211> LENGTH: 362
<212> TYPE: DNA
<213> ORGANISM: Artificial Sequence
<220> FEATURE:
<223> OTHER INFORMATION: synthetic sequence

<400> SEQUENCE: 44

| gaggtgcagc tgttggagtc tgggggaggc ttggtacagc ctggggggtc cctgagactc | 60 |
| tcctgtgcag cctctggatt cactttcagt agttatacca tgtcttgggt ccgccaggct | 120 |
| ccagggaagg ggctggagtg ggtctcagtc attagtagtg gtggtgattc cgcctactat | 180 |
| ccagacagtg tgcagggccg gttcaccatc tccagagaca attccaagaa cacgctgtat | 240 |
| ctgcaaatga acagcctgag agccgaggac acggccgtat attactgtgc gaaagagcac | 300 |
| tacggtacta gtcactttgc ttactggggc caaggaaccc tggtcaccgt ctcctcagca | 360 |
| tc | 362 |

<210> SEQ ID NO 45
<211> LENGTH: 362
<212> TYPE: DNA
<213> ORGANISM: Artificial Sequence
<220> FEATURE:
<223> OTHER INFORMATION: synthetic sequence

<400> SEQUENCE: 45

| gaggtgcagc tgttggagtc tgggggaggc ttggtacagc ctggggggtc cctgagactc | 60 |
| tcctgtgcag cctctggatt cactttcagt agttatacca tgtcttgggt ccgccaggct | 120 |
| ccagggaagg ggctggagtg ggtctcagtc attagtagtg gtggtaattc cgcctactat | 180 |
| ccagacagtg tgcagggccg gttcaccatc tccagagaca attccaagaa cacgctgtat | 240 |
| ctgcaaatga acagcctgag agccgaggac acggccgtat attactgtgc gaaagagcac | 300 |
| tacggtacta gtcactttgc ttactggggc caaggaaccc tggtcaccgt ctcctcagca | 360 |
| tc | 362 |

<210> SEQ ID NO 46
<211> LENGTH: 362
<212> TYPE: DNA
<213> ORGANISM: Artificial Sequence
<220> FEATURE:
<223> OTHER INFORMATION: synthetic sequence

<400> SEQUENCE: 46

```
gaggtgcagc tgttggagtc tgggggaggc ttggtacagc ctggggggtc cctgagactc    60
tcctgtgcag cctctggatt cactttcagt agttatacca tgtcttgggt ccgccaggct   120
ccagggaagg ggctggagtg ggtctcagtc attagtagtg gtggtaatta cgcctactat   180
ccagacagtg tgcagggccg gttcaccatc tccagagaca attccaagaa cacgctgtat   240
ctgcaaatga acagcctgag agccgaggac acggccgtat attactgtgc gaaagagcac   300
tacggtacta gtcactttgc ttactggggc caaggaaccc tggtcaccgt ctcctcagca   360
tc                                                                  362
```

<210> SEQ ID NO 47
<211> LENGTH: 362
<212> TYPE: DNA
<213> ORGANISM: Artificial Sequence
<220> FEATURE:
<223> OTHER INFORMATION: synthetic sequence

<400> SEQUENCE: 47

```
gaggtgcagc tgttggagtc tgggggaggc ttggtacagc ctggggggtc cctgagactc    60
tcctgtgcag cctctggatt cactttcagt agttatacca tgtcttgggt ccgccaggct   120
ccagggaagg ggctggagtg ggtctcagtc attagtagtg gtggtgattc cacctactat   180
ccagacagtg tgcagggccg gttcaccatc tccagagaca attccaagaa cacgctgtat   240
ctgcaaatga acagcctgag agccgaggac acggccgtat attactgtgc gaaagagcac   300
tacggtacta gtcactttgc ttactggggc caaggaaccc tggtcaccgt ctcctcagca   360
tc                                                                  362
```

<210> SEQ ID NO 48
<211> LENGTH: 362
<212> TYPE: DNA
<213> ORGANISM: Artificial Sequence
<220> FEATURE:
<223> OTHER INFORMATION: synthetic sequence

<400> SEQUENCE: 48

```
gaggtgcagc tgttggagtc tgggggaggc ttggtacagc ctggggggtc cctgagactc    60
tcctgtgcag cctctggatt cactttcagt agttatacca tgtcttgggt ccgccaggct   120
ccagggaagg ggctggagtg ggtctcagtc attagtagtg gtggtaattc cgcctactat   180
ccagacagtg tgcagggccg gttcaccatc tccagagaca attccaagaa cacgctgtat   240
ctgcaaatga acagcctgag agccgaggac acggccgtat attactgtgc gaaagagtac   300
tacggttcta gtcactttgc ttactggggc caaggaaccc tggtcaccgt ctcctcagca   360
tc                                                                  362
```

<210> SEQ ID NO 49
<211> LENGTH: 360
<212> TYPE: DNA
<213> ORGANISM: Artificial Sequence
<220> FEATURE:
<223> OTHER INFORMATION: synthetic sequence

<400> SEQUENCE: 49

```
gacgtgaagc tggtggagtc tgggggaggc ttagtgaagc ctggagggtc cctgaaagtc    60
tcctgtgcag cctctggatt cactttcagt agctatacca tgtcttgggt tcgccagact   120
ccggagaaga ggctggagtg ggtcgcagtc attagtagtg gtggtaattc cacctactat   180
```

```
ccagacagtg tgaagggccg attcaccatc tccagagaca atgccaagaa caccctgtac    240
ctgcaaatga gcagtctgaa gtctgaggac acagccatgt attactgtac aagagagcac    300
tacggtagta gtcactttgc ttactggggc caagggactc tggtcactgt ctctgcagcc    360
```

<210> SEQ ID NO 50
<211> LENGTH: 360
<212> TYPE: DNA
<213> ORGANISM: Artificial Sequence
<220> FEATURE:
<223> OTHER INFORMATION: synthetic sequence

<400> SEQUENCE: 50

```
gaggtgcagc tgttggagtc tgggggaggc ttggtacagc ctggggggtc cctgagactc     60
tcctgtgcag cctctggatt cactttcagt agctataccA tgtcttgggt ccgccaggct    120
ccagggaagg ggctggagtg ggtctcagtc attagtagtg gtggtaattc cacctactat    180
ccagacagtg tgaagggccg gttcaccatc tccagagaca attccaagaa cacgctgtat    240
ctgcaaatga acagcctgag agccgaggac acggccgtat attactgtgc gaaagagcac    300
tacggtagta gtcactttgc ttactggggc caaggaaccc tggtcaccgt ctcctcagca    360
```

<210> SEQ ID NO 51
<211> LENGTH: 360
<212> TYPE: DNA
<213> ORGANISM: Artificial Sequence
<220> FEATURE:
<223> OTHER INFORMATION: synthetic sequence

<400> SEQUENCE: 51

```
gaggtgcagc tgttggagtc tgggggaggc ttggtacagc ctggggggtc cctgagactc     60
tcctgtgcag cctctggatt cactttcagt agctatacCc tgtcttgggt ccgccaggct    120
ccagggaagg ggctggagtg ggtctcagtc attagtagtg gtggtaatta cgcctactat    180
ccagacagtg tgcagggccg gttcaccatc tccagagaca attccaagaa cacgctgtat    240
ctgcaaatga acagcctgag agccgaggac acggccgtat attactgtgc gaaagagcac    300
tacggtacta gtcactttgc ttactggggc caaggaaccc tggtcaccgt ctcctcagca    360
```

<210> SEQ ID NO 52
<211> LENGTH: 351
<212> TYPE: DNA
<213> ORGANISM: Artificial Sequence
<220> FEATURE:
<223> OTHER INFORMATION: synthetic sequence

<400> SEQUENCE: 52

```
gaagtgatgc tggtggagtc tgggggaggc ttagtgaagc ctggagggtc cctgaaactc     60
tcctgtgcag cctctggatt cactttcagt agctatgaca tgtcttgggt tcgccagact    120
ccggagaaga ggctggagtg ggtcgcaacc attagtggtg gtggtagtta cacctactat    180
caagacagtg tgaagggccg attcaccatc tccagagaca atgccaagaa caccctgtac    240
ctgcaaatga gcagtctgag gtctgaggac acggccatgt attactgtgc ctcccctta    300 tatgctatgg actactgggg tcaaggaacc tcagtcaccg tctcctcagc a              351
```

<210> SEQ ID NO 53
<211> LENGTH: 351
<212> TYPE: DNA
<213> ORGANISM: Artificial Sequence
<220> FEATURE:
<223> OTHER INFORMATION: synthetic sequence

<400> SEQUENCE: 53

```
gaggtgcagc tgttggagtc tgggggaggc ttggtacagc ctgggggtc cctgagactc    60
tcctgtgcag cctctggatt cactttcagt agctatgaca tgtcttgggt ccgccaggct   120
ccagggaagg ggctggagtg ggtctcaacc attagtggtg gtggtagtta cacctactat   180
caagacagtg tgaaggggcg gttcaccatc tccagagaca attccaagaa cacgctgtat   240
ctgcaaatga acagcctgag agccgaggac acggccgtat attactgtgc gtccccttac   300
tatgctatgg actactgggg gcaagggacc acggtcaccg tctcctcagc a            351
```

<210> SEQ ID NO 54
<211> LENGTH: 351
<212> TYPE: DNA
<213> ORGANISM: Artificial Sequence
<220> FEATURE:
<223> OTHER INFORMATION: synthetic sequence

<400> SEQUENCE: 54

```
gaggtgcagc tgttggagtc tgggggaggc ttggtacagc ctgggggtc cctgagactc    60
tcctgtgcag cctctggatt cactttcagt agctatgaca tgtcttgggt ccgccaggct   120
ccagggaagg ggctggagtg ggtctcaacc attagtggtg gtggtagtta cacctactat   180
caagacagtg tgaaggggcg gttcatcatc tccagagaca attccaagaa cacgctgtat   240
ctgcaaatga acagcctgag agccgaggac acggccgtat attactgtgc gtccccttac   300
tatgctatgg actactgggg gcaagggacc acggtcaccg tctcctcagc a            351
```

<210> SEQ ID NO 55
<211> LENGTH: 351
<212> TYPE: DNA
<213> ORGANISM: Artificial Sequence
<220> FEATURE:
<223> OTHER INFORMATION: synthetic sequence

<400> SEQUENCE: 55

```
gaggtgcagc tgttggagtc tgggggaggc ttggtacagc ctgggggtc cctgagactc    60
tcctgtgcag cctctggatt cactttcagt agctatgaca tgtcttgggt ccgccgggct   120
ccagggaagg ggctggagtg ggtctcaacc attagtggtg gtggtagtta cacctactat   180
caagacagtg tgaaggggcg gttcaccatc tccagagaca attccaagaa cacgctgtat   240
ctgcaaatga acagcctgag agccgaggac acggccgtat attactgtgc gtccccttac   300
tatgctatgg actactgggg gcaagggacc acggtcaccg tctcctcagc a            351
```

<210> SEQ ID NO 56
<211> LENGTH: 336
<212> TYPE: DNA
<213> ORGANISM: Artificial Sequence
<220> FEATURE:
<223> OTHER INFORMATION: synthetic sequence

<400> SEQUENCE: 56

```
gacattgtgc tgacccaatc tccagcttct ttggctgtgt ctctagggca gagggccacc    60
atctcctgca gagccagcga aagtgttgat aattttggca ttagttttat gagctggttc   120
caacagaaac caggacagcc acccaaactc ctcatctatg ctgcatccaa cccaggatcc   180
ggggtccctg ccaggtttag tggcagtgta tctgggacag acttcagcct caacatccat   240
cctatggagg aggatgatgc tgcaatgtat ttctgtcagc aaagtaagga ggttccgtac   300
```

```
acgttcggag gggggaccaa gctggaaata aaacgg                              336
```

<210> SEQ ID NO 57
<211> LENGTH: 336
<212> TYPE: DNA
<213> ORGANISM: Artificial Sequence
<220> FEATURE:
<223> OTHER INFORMATION: synthetic sequence

<400> SEQUENCE: 57

```
gaaattgtgt tgacacagtc tccagccacc ctgtctttgt ctccagggga aagagccacc    60
ctctcctgca gagccagcga aagtgttgat aattttggca ttagttttat gagctggtac   120
caacagaaac ctggccaggc tcccaggctc ctcatctatg ctgcatccaa cccaggatcc   180
ggcatcccag ccaggttcag tggcagtggg tctgggacag acttcactct caccatcagc   240
agcctagagc ctgaagattt tgcagtttat tactgtcagc aaagtaagga ggttccgtac   300
acgtttggcc aggggaccaa gctggagatc aaacgg                             336
```

<210> SEQ ID NO 58
<211> LENGTH: 336
<212> TYPE: DNA
<213> ORGANISM: Artificial Sequence
<220> FEATURE:
<223> OTHER INFORMATION: synthetic sequence

<400> SEQUENCE: 58

```
gacattgtgc tgacccaatc tccagattct ttggctgtgt ctctagggct gagggccacc    60
atctcctgca gagccagcga aagtgttgat aaatatggca ttagttttat gagctggttc   120
caacagaaac caggacagcc acccaaactc ctcatctatg ctgcatccaa ccaaggatcc   180
ggggtccctg ccaggtttag tggcagtggg tctgggacag acttcagcct caacatccat   240
cctatggagg aggatgatac tgcaatgtat ttctgtcagc aaagtaagga ggttccgtac   300
acgttcggag gggggaccaa gctggaaata aaacgg                             336
```

<210> SEQ ID NO 59
<211> LENGTH: 336
<212> TYPE: DNA
<213> ORGANISM: Artificial Sequence
<220> FEATURE:
<223> OTHER INFORMATION: synthetic sequence

<400> SEQUENCE: 59

```
gacatcgtga tgacccagtc tccagactcc ctggctgtgt ctctgggcga gagggccacc    60
atcaactgca gagccagcga aagtgttgat aaatatggca ttagttttat gagctggtac   120
cagcagaaac caggacagcc tcctaagctg ctcatttacg ctgcatccaa ccaaggatcc   180
ggggtccctg accgattcag tggcagcggg tctgggacag atttcactct caccatcagc   240
agcctgcagg ctgaagatgt ggcagtttat tactgtcagc aaagtaagga ggttccgtac   300
acgtttggcc aggggaccaa gctggagatc aaacgg                             336
```

<210> SEQ ID NO 60
<211> LENGTH: 336
<212> TYPE: DNA
<213> ORGANISM: Artificial Sequence
<220> FEATURE:
<223> OTHER INFORMATION: synthetic sequence

<400> SEQUENCE: 60

```
gacatcgtga tgacccagtc tccagactcc ctggctgtgt ctctgggcga gagggccacc    60
```

```
atcaactgca gagccagcga aagtgttgat aaatatggca ttactttat gagctggtac    120 cagcagaaac caggacagcc tcctaagctg ctcatttacg ctgcatccaa ccaaggatcc    180
ggggtccctg accgattcag tggcagcggg tctgggacag atttcactct caccatcagc    240
agcctgcagg ctgaagatgt ggcagtttat tactgtcagc aaagtaagga ggttccgtac    300
acgtttggcc aggggaccaa gctggagatc aaacgg                              336

<210> SEQ ID NO 61
<211> LENGTH: 324
<212> TYPE: DNA
<213> ORGANISM: Artificial Sequence
<220> FEATURE:
<223> OTHER INFORMATION: synthetic sequence

<400> SEQUENCE: 61
gacattgtga tgacccagtc tcacaaattc atgtccacat cagtaggaga cagggtcagc     60
atcacctgca aggccagtca ggatgtgggt actgctgtag cctggtatca acagaaacca    120
gggcaatctc ctaaactact gatttactgg gcatccaccc ggcacactgg agtccctgat    180
cgcttcacag gcagtggatc tgggacagat ttcactctca ccattagcaa tgtgcagtct    240
gaagacttgg cagattattt ctgtcagcat tatagcagct atccgtggac gttcggtgga    300
ggcaccaaac tggaaatcaa acgg                                           324

<210> SEQ ID NO 62
<211> LENGTH: 324
<212> TYPE: DNA
<213> ORGANISM: Artificial Sequence
<220> FEATURE:
<223> OTHER INFORMATION: synthetic sequence

<400> SEQUENCE: 62
gacatccagt tgacccagtc tccatccttc ctgtctgcat ctgtaggaga cagagtcacc     60
atcacttgca aggccagtca ggatgtgggt actgctgtag cctggtatca gcaaaaacca    120
gggaaagccc ctaagctcct gatctattgg gcatccaccc ggcacactgg ggtcccatca    180
aggttcagcg gcagtggatc tgggacagaa ttcactctca caatcagcag cctgcagcct    240
gaagattttg caacttatta ctgtcagcat tatagcagct atccgtggac gtttggccag    300
gggaccaagc tggagatcaa acgg                                           324

<210> SEQ ID NO 63
<211> LENGTH: 324
<212> TYPE: DNA
<213> ORGANISM: Artificial Sequence
<220> FEATURE:
<223> OTHER INFORMATION: synthetic sequence

<400> SEQUENCE: 63
gacatccagt tgacccagtc tccatccttc ctgtctgcat atgtaggaga cagagtcacc     60
atcacttgca aggccagtca ggatgtgggt actgctgtag cctggtatca gcaaaaacca    120
gggaaagccc ctaagctcct gatctattgg gcatccaccc tgcacactgg ggtcccatca    180
aggttcagcg gcagtggatc tgggacagaa ttcactctca caatcagcag cctgcagcct    240
gaagattttg caacttatta ctgtcagcat tatagcagct atccgtggac gtttggccag    300
gggaccaagc tggagatcaa acgg                                           324

<210> SEQ ID NO 64
```

```
<211> LENGTH: 324
<212> TYPE: DNA
<213> ORGANISM: Artificial Sequence
<220> FEATURE:
<223> OTHER INFORMATION: synthetic sequence

<400> SEQUENCE: 64
gacatccagt tgacccagtc tccatccttc ctgtctgcat atgtaggaga cagagtcacc      60
atcacttgca aggccagtca ggatgtgggt actgctgtag cctggtatca gcaaaaacca     120
gggaaagccc ctaagctcct gatctattgg gcatccaccc ggcacactgg ggtcccatca     180
aggttcagcg gcagtggatc tgggacagaa ttcactctca caatcagcag cctgcagcct     240
gaagattttg caacttatta ctgtcagcat tataacagct atccgtggac gtttggccag     300
gggaccaagc tggagatcaa acgg                                            324
```

ANTIBODIES DIRECTED AGAINST PROGRAMMED DEATH-1 (PD-1)

This application is a continuation of U.S. patent application Ser. No. 14/888,557, filed on Nov. 2, 2015, now U.S. Pat. No. 9,815,897, which is the National Stage of International Application No. PCT/US2014/036525, filed on May 2, 2014, which claims the benefit of U.S. Provisional Application No. 61/818,755, filed on May 2, 2013, each of which is incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 45,217 Byte ASCII (Text) file named "727424_ST25.TXT," created on Dec. 20, 2016.

BACKGROUND OF THE INVENTION

Programmed Death 1 (PD-1) (also known as Programmed Cell Death 1) is a type I transmembrane protein of 268 amino acids originally identified by subtractive hybridization of a mouse T cell line undergoing apoptosis (Ishida et al., *Embo J.*, 11: 3887-95 (1992)). PD-1 is a member of the CD28/CTLA-4 family of T-cell regulators, and is expressed on activated T-cells, B-cells, and myeloid lineage cells (Greenwald et al., *Annu. Rev. Immunol.*, 23: 515-548 (2005); and Sharpe et al., *Nat. Immunol.*, 8: 239-245 (2007)).

Two ligands for PD-1 have been identified, PD ligand 1 (PD-L1) and PD ligand 2 (PD-L2), both of which belong to the B7 protein superfamily (Greenwald et al., supra). PD-L1 is expressed in a variety of cell types, including cells of the lung, heart, thymus, spleen, and kidney (see, e.g., Freeman et al., *J. Exp. Med.*, 192(7): 1027-1034 (2000); and Yamazaki et al., *J. Immunol.*, 169(10): 5538-5545 (2002)). PD-L1 expression is upregulated on macrophages and dendritic cells (DCs) in response to lipopolysaccharide (LPS) and GM-CSF treatment, and on T-cells and B-cells upon signaling via T-cell and B-cell receptors. PD-L1 also is expressed in a variety of murine tumor cell lines (see, e.g., Iwai et al., *Proc. Natl. Acad. Sci. USA*, 99(19): 12293-12297 (2002); and Blank et al., *Cancer Res.*, 64(3): 1140-1145 (2004)). In contrast, PD-L2 exhibits a more restricted expression pattern and is expressed primarily by antigen presenting cells (e.g., dendritic cells and macrophages), and some tumor cell lines (see, e.g., Latchman et al., *Nat. Immunol.*, 2(3): 261-238 (2001)). High PD-L1 expression in tumors, whether on the tumor cell, stroma, or other cells within the tumor microenvironment, correlates with poor clinical prognosis, presumably by inhibiting effector T cells and upregulating regulatory T cells (Treg) in the tumor.

PD-1 negatively regulates T-cell activation, and this inhibitory function is linked to an immunoreceptor tyrosine-based switch motif (ITSM) in the cytoplasmic domain (see, e.g., Greenwald et al., supra; and Parry et al., *Mol. Cell. Biol.*, 25: 9543-9553 (2005)). PD-1 deficiency can lead to autoimmunity. For example, C57BL/6 PD-1 knockout mice have been shown to develop a lupus-like syndrome (see, e.g., Nishimura et al., *Immunity*, 11: 141-1151 (1999)). In humans, a single nucleotide polymorphism in the PD-1 gene is associated with higher incidences of systemic lupus erythematosus, type 1 diabetes, rheumatoid arthritis, and progression of multiple sclerosis (see, e.g., Nielsen et al., *Tissue Antigens*, 62(6): 492-497 (2003); Bertsias et al., *Arthritis Rheum.*, 60(1): 207-218 (2009); Ni et al., *Hum. Genet.*, 121(2): 223-232 (2007); Tahoori et al., *Clin. Exp. Rheumatol.*, 29(5): 763-767 (2011); and Kroner et al., *Ann. Neurol.*, 58(1): 50-57 (2005)). Abnormal PD-1 expression also has been implicated in T-cell dysfunctions in several pathologies, such as tumor immune evasion and chronic viral infections (see, e.g., Barber et al., *Nature*, 439: 682-687 (2006); and Sharpe et al., supra).

Recent studies demonstrate that T-cell suppression induced by PD-1 also plays a role in the suppression of anti-tumor immunity. For example, PD-L1 is expressed on a variety of human and mouse tumors, and binding of PD-1 to PD-L1 on tumors results in T-cell suppression and tumor immune evasion and protection (Dong et al., *Nat. Med.*, 8: 793-800 (2002)). Expression of PD-L1 by tumor cells has been directly associated with their resistance to lysis by anti-tumor T-cells in vitro (Dong et al., supra; and Blank et al., *Cancer Res.*, 64: 1140-1145 (2004)). PD-1 knockout mice are resistant to tumor challenge (Iwai et al., *Int. Immunol.*, 17: 133-144 (2005)), and T-cells from PD-1 knockout mice are highly effective in tumor rejection when adoptively transferred to tumor-bearing mice (Blank et al., supra). Blocking PD-1 inhibitory signals using a monoclonal antibody can potentiate host anti-tumor immunity in mice (Iwai et al., supra; and Hirano et al., *Cancer Res.*, 65: 1089-1096 (2005)), and high levels of PD-L1 expression in tumors are associated with poor prognosis for many human cancer types (Hamanishi et al., *Proc. Natl. Acad. Sci. USA*, 104: 3360-335 (2007), Brown et al., *J. Immunol.*, 170: 1257-1266 (2003); and Flies et al., *Yale Journal of Biology and Medicine*, 84(4): 409-421 (2011)).

In view of the foregoing, strategies for inhibiting PD-1 activity to treat various types of cancer and for immunopotentiation (e.g., to treat infectious diseases) have been developed (see, e.g., Ascierto et al., *Clin. Cancer. Res.*, 19(5): 1009-1020 (2013)). In this respect, monoclonal antibodies targeting PD-1 have been developed for the treatment of cancer (see, e.g., Weber, *Semin. Oncol.*, 37(5): 430-4309 (2010); and Tang et al., *Current Oncology Reports*, 15(2): 98-104 (2013)). For example, nivolumab (also known as BMS-936558) produced complete or partial responses in non-small-cell lung cancer, melanoma, and renal-cell cancer in a Phase I clinical trial (see, e.g., Topalian, *New England J. Med.*, 366: 2443-2454 (2012)), and is currently in Phase III clinical trials. MK-3575 is a humanized monoclonal antibody directed against PD-1 that has shown evidence of antitumor activity in Phase I clinical trials (see, e.g., Patnaik et al., 2012 *American Society of Clinical Oncology (ASCO) Annual Meeting*, Abstract #2512). In addition, recent evidence suggests that therapies which target PD-1 may enhance immune responses against pathogens, such as HIV (see, e.g., Porichis et al., *Curr. HIV/AIDS Rep.*, 9(1): 81-90 (2012)). Despite these advances, however, the efficacy of these potential therapies in humans may be limited.

Therefore, there is a need for a PD-1-binding agent (e.g., an antibody) that binds PD-1 with high affinity and effectively neutralizes PD-1 activity. The invention provides such PD-1-binding agents.

BRIEF SUMMARY OF THE INVENTION

The invention provides an isolated immunoglobulin heavy chain polypeptide which comprises a complementarity determining region 1 (CDR) amino acid sequence of SEQ ID NO: 1, a CDR2 amino acid sequence of SEQ ID NO: 2, and a CDR3 amino acid sequence of SEQ ID NO: 3, wherein optionally (a) residue 9 of SEQ ID NO: 1 is replaced with a different amino acid residue, (b) one or more of residues 7, 8, and 9 of SEQ ID NO: 2 is replaced with a different amino acid residue, (c) one or more of residues 1, 2, and 5 of SEQ ID NO: 3 is replaced with a different amino acid residue, or (d) any combination of (a)-(c).

The invention provides an isolated immunoglobulin heavy chain polypeptide which comprises a complementarity determining region 1 (CDR) amino acid sequence of SEQ ID NO: 12, a CDR2 amino acid sequence of SEQ ID NO: 13, and a CDR3 amino acid sequence of SEQ ID NO: 14, wherein optionally (a) residue 9 of SEQ ID NO: 12 is replaced with a different amino acid residue, (b) residue 8 and/or residue 9 of SEQ ID NO: 13 is replaced with a different amino acid residue, (c) residue 5 of SEQ ID NO: 14 is replaced with a different amino acid residue, or (d) any combination of (a)-(c).

The invention provides an isolated immunoglobulin heavy chain polypeptide which comprises a complementarity determining region 1 (CDR) amino acid sequence of SEQ ID NO: 19, a CDR2 amino acid sequence of SEQ ID NO: 20, and a CDR3 amino acid sequence of SEQ ID NO: 21.

The invention also provides an isolated immunoglobulin heavy chain polypeptide which comprises an amino acid sequence that is at least 90% identical to any one of SEQ ID NOs: 4-11, SEQ ID NOs: 15-18, and SEQ ID NOs: 22-25.

The invention provides an isolated immunoglobulin light chain polypeptide which comprises a complementarity determining region 1 (CDR) amino acid sequence of SEQ ID NO: 26 and a CDR2 amino acid sequence of SEQ ID NO: 27.

The invention provides an isolated immunoglobulin light chain polypeptide which comprises a complementarity determining region 1 (CDR) amino acid sequence of SEQ ID NO: 30 and a CDR2 amino acid sequence of SEQ ID NO: 31, wherein optionally residue 12 of SEQ ID NO: 30 is replaced with a different amino acid residue.

The invention provides an isolated immunoglobulin light chain polypeptide which comprises a complementarity determining region 1 (CDR) amino acid sequence of SEQ ID NO: 35, a CDR2 amino acid sequence of SEQ ID NO: 36, and a CDR3 amino acid sequence of SEQ ID NO: 37, wherein optionally (a) residue 5 of SEQ ID NO: 36 is replaced with a different amino acid residue, and/or (b) residue 4 of SEQ ID NO: 37 is replaced with a different amino acid residue.

The invention provides an isolated immunoglobulin light chain polypeptide which comprises an amino acid sequence that is at least 90% identical to SEQ ID NO: 28, SEQ ID NO: 29, SEQ ID NO: 32, SEQ ID NO: 33, SEQ ID NO: 34, SEQ ID NO: 38, SEQ ID NO: 39, SEQ ID NO: 40, or SEQ ID NO: 41.

In addition, the invention provides isolated or purified nucleic acid sequences encoding the foregoing immunoglobulin polypeptides, vectors comprising such nucleic acid sequences, isolated PD-1-binding agents comprising the foregoing immunoglobulin polypeptides, nucleic acid sequences encoding such PD-1-binding agents, vectors comprising such nucleic acid sequences, isolated cells comprising such vectors, compositions comprising such PD-1-binding agents or such vectors with a pharmaceutically acceptable carrier, and methods of treating cancer or infectious diseases in mammals by administering effective amounts of such compositions to mammals.

BRIEF DESCRIPTION THE DRAWINGS

DETAILED DESCRIPTION OF THE INVENTION

Figure 1:
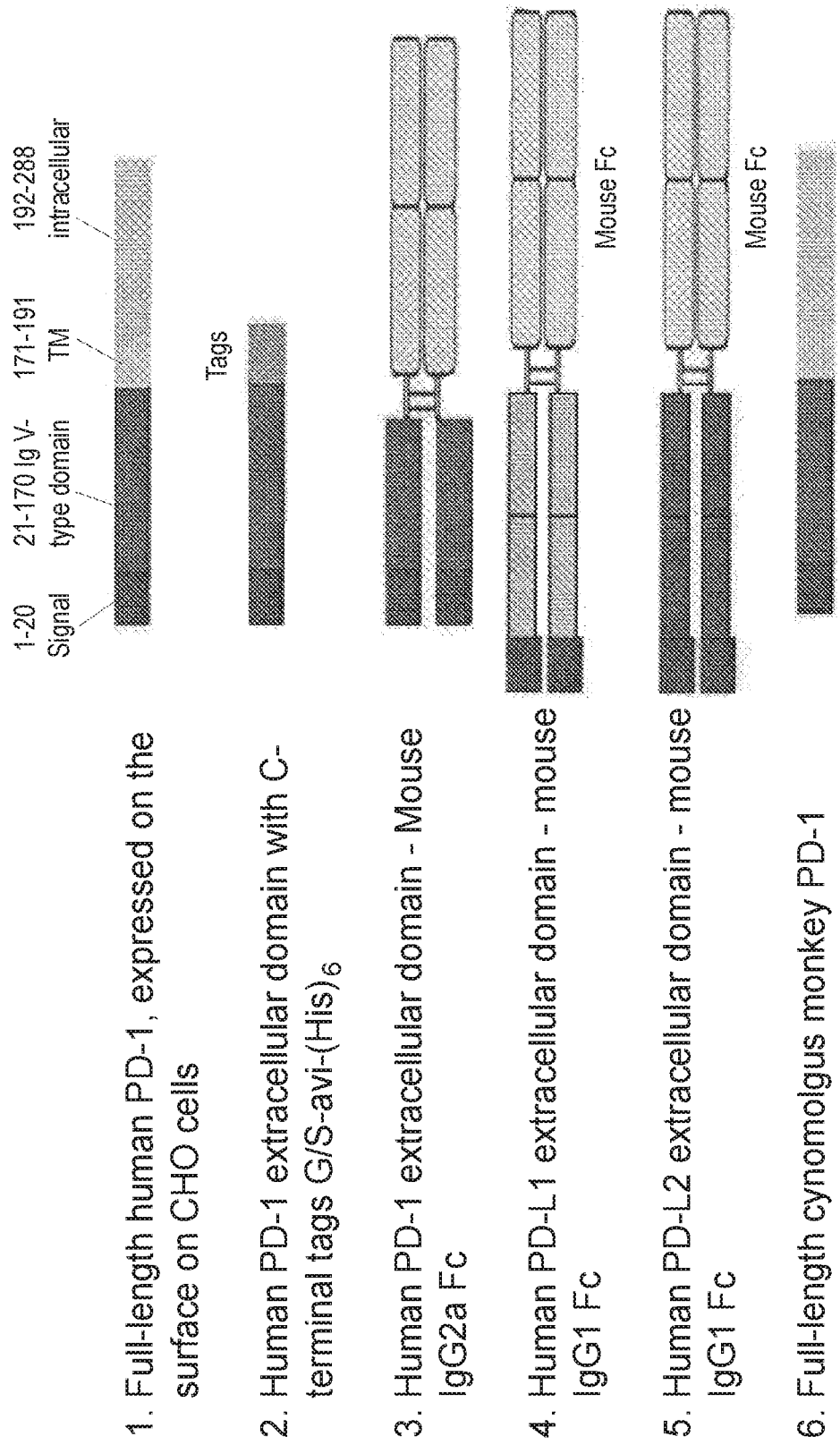
FIG. 1 is a diagram which schematically depicts different PD-1 antigen constructs utilized to generate anti-PD-1 monoclonal antibodies as described in Example 1.

The invention provides an isolated immunoglobulin heavy chain polypeptide and/or an isolated immunoglobulin light chain polypeptide, or a fragment (e.g., antigen-binding fragment) thereof. The term "immunoglobulin" or "antibody," as used herein, refers to a protein that is found in blood or other bodily fluids of vertebrates, which is used by the immune system to identify and neutralize foreign objects, such as bacteria and viruses. The polypeptide is "isolated" in that it is removed from its natural environment. In a preferred embodiment, an immunoglobulin or antibody is a protein that comprises at least one complementarity determining region (CDR). The CDRs form the "hypervariable region" of an antibody, which is responsible for antigen binding (discussed further below). A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_H1$, $C_H2$, and $C_H3$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), *Immunobiology*, 5th Ed., Garland Publishing, New York, N.Y. (2001)).

The framework regions are connected by three complementarity determining regions (CDRs). As discussed above, the three CDRs, known as CDR1, CDR2, and CDR3, form the "hypervariable region" of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

The isolated immunoglobulin heavy chain polypeptide and the isolated immunoglobulin light chain polypeptide of the invention desirably bind to PD-1. As discussed above, programmed death 1 (PD-1) (also known as programmed cell death 1) is a 268 amino acid type I transmembrane protein (Ishida et al., supra). PD-1 is a member of the CD28/CTLA-4 family of T-cell regulators and is expressed on activated T-cells, B-cells, and myeloid lineage cells (Greenwald et al., supra; and Sharpe et al., supra). PD-1 includes an extracellular IgV domain followed by short extracellular stalk, a transmembrane region and an intracellular tail. The intracellular tail contains two phosphorylation sites located in an immunoreceptor tyrosine-based inhibitory motif and an immunoreceptor tyrosine-based switch motif, which play a role in the ability of PD-1 to negatively regulate T-cell receptor signaling (see, e.g., Ishida et al., supra; and Blank et al., supra). The inventive isolated immunoglobulin heavy chain polypeptide and the inventive isolated immunoglobulin light chain polypeptide can form an agent that binds to PD-1 and another antigen, resulting in a "dual reactive" binding agent (e.g., a dual reactive antibody). For example, the agent can bind to PD-1 and to another negative regulator of the immune system such as, for example, lymphocyte-activation gene 3 (LAG-3) and/or T-cell immunoglobulin domain and mucin domain 3 protein (TIM-3).

Antibodies which bind to PD-1, and components thereof, are known in the art (see, e.g., U.S. Pat. No. 8,168,757; Topalian et al., supra; and Patnaik et al., supra). Anti-PD-1 antibodies also are commercially available from sources such as, for example, Abcam (Cambridge, Mass.).

An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

The invention provides an immunoglobulin heavy chain polypeptide that comprises a complementarity determining region 1 (CDR) amino acid sequence of SEQ ID NO: 1, a CDR2 amino acid sequence of SEQ ID NO: 2, and a CDR3 amino acid sequence of SEQ ID NO: 3. In one embodiment of the invention, the isolated immunoglobulin heavy chain polypeptide comprises, consists of, or consists essentially of a complementarity determining region 1 (CDR) amino acid sequence of SEQ ID NO: 1, a CDR2 amino acid sequence of SEQ ID NO: 2, and a CDR3 amino acid sequence of SEQ ID NO: 3, wherein optionally (a) residue 9 of SEQ ID NO: 1 is replaced with a different amino acid residue, (b) one or more of residues 7, 8, and 9 of SEQ ID NO: 2 is replaced with a different amino acid residue, (c) one or more of residues 1, 2, and 5 of SEQ ID NO: 3 is replaced with a different amino acid residue, or (d) any combination of (a)-(c). When the inventive immunoglobulin heavy chain polypeptide consists essentially of a CDR1 amino acid sequence of SEQ ID NO: 1, a CDR2 amino acid sequence of SEQ ID NO: 2, and a CDR3 amino acid sequence of SEQ ID NO: 3 and optional amino acid replacements, additional components can be included in the polypeptide that do not materially affect the polypeptide (e.g., protein moieties such as biotin that facilitate purification or isolation). When the inventive immunoglobulin heavy chain polypeptide consists of a CDR1 amino acid sequence of SEQ ID NO: 1, a CDR2 amino acid sequence of SEQ ID NO: 2, and a CDR3 amino acid sequence of SEQ ID NO: 3 and optional amino acid replacements, the polypeptide does not comprise any additional components (i.e., components that are not endogenous to the inventive immunoglobulin heavy chain polypeptide).

In one embodiment of the invention, the isolated immunoglobulin polypeptide comprises a CDR1 amino acid sequence of SEQ ID NO: 1, a CDR2 amino acid sequence of SEQ ID NO: 2, and a CDR3 amino acid sequence of SEQ ID NO: 3, except that (a) residue 9 of SEQ ID NO: 1 is replaced with a different amino acid residue, (b) one or more of residues 7, 8, and 9 of SEQ ID NO: 2 is replaced with a different amino acid residue, (c) one or more of residues 1, 2, and 5 of SEQ ID NO: 3 is replaced with a different amino acid residue, or (d) any combination of (a)-(c). For example, the isolated immunoglobulin heavy chain polypeptide can comprise a CDR1 amino acid sequence of SEQ ID NO: 1, a CDR2 amino acid sequence of SEQ ID NO: 2, and a CDR3 amino acid sequence of SEQ ID NO: 3, except that residue 9 of SEQ ID NO: 1 is replaced with a different amino acid residue and one or more of residues 7, 8, and 9 of SEQ ID NO: 2 is replaced with a different amino acid residue. Alternatively, the isolated immunoglobulin heavy chain polypeptide can comprise a CDR1 amino acid sequence of SEQ ID NO: 1, a CDR2 amino acid sequence of SEQ ID NO: 2, and a CDR3 amino acid sequence of SEQ ID NO: 3, except that residue 9 of SEQ ID NO: 1 is replaced with a different amino acid residue, one or more of residues 7, 8, and 9 of SEQ ID NO: 2 is replaced with a different amino acid residue, and one or more of residues 1, 2, and 5 of SEQ ID NO: 3 is replaced with a different amino acid residue. In another embodiment, the isolated immunoglobulin heavy chain polypeptide can comprise a CDR1 amino acid sequence of SEQ ID NO: 1, a CDR2 amino acid sequence of SEQ ID NO: 2, and a CDR3 amino acid sequence of SEQ ID NO: 3, except that one or more of residues 1, 2, and 5 of SEQ ID NO: 3 is replaced with a different amino acid residue. Each of residue 9 of SEQ ID NO: 1, residues 7, 8, and 9 of SEQ ID NO: 2, and residues 1, 2, and 5 of SEQ ID NO: 3 can be replaced with any suitable amino acid residue that can be the same or different in each position. For example, the amino acid residue of a first position can be replaced with a first different amino acid residue, and the amino acid residue of a second position can be replaced with a second different amino acid residue, wherein the first and second different amino acid residues are the same or different.

In one embodiment, the isolated immunoglobulin heavy chain polypeptide comprises a CDR1 amino acid sequence of SEQ ID NO: 1, a CDR2 amino acid sequence of SEQ ID NO: 2, and a CDR3 amino acid sequence of SEQ ID NO: 3, except that residue 9 of SEQ ID NO: 1 is replaced with a methionine (M) residue. In another embodiment, the isolated immunoglobulin heavy chain polypeptide comprises a CDR1 amino acid sequence of SEQ ID NO: 1, a CDR2 amino acid sequence of SEQ ID NO: 2, and a CDR3 amino acid sequence of SEQ ID NO: 3, except that (a) residue 7 of SEQ ID NO: 2 is replaced with an asparagine (N) residue, (b) residue 8 of SEQ ID NO: 2 is replaced with a serine (S) residue, (c) residue 9 of SEQ ID NO: 2 is replaced with a threonine (T) residue, or (d) any combination of (a)-(c). In another embodiment, the isolated immunoglobulin heavy chain polypeptide comprises a CDR1 amino acid sequence of SEQ ID NO: 1, a CDR2 amino acid sequence of SEQ ID NO: 2, and a CDR3 amino acid sequence of SEQ ID NO: 3, except that (a) residue 1 of SEQ ID NO: 3 is replaced with a glutamic acid (E) residue, (b) residue 2 of SEQ ID NO: 3 is replaced with a tyrosine (Y) residue, (c) residue 5 of SEQ ID NO: 3 is replaced with a serine (S) residue, or (d) any combination of (a)-(c).

Exemplary immunoglobulin heavy chain polypeptides as described above can comprise any one of the following amino acid sequences: SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

The invention provides an isolated immunoglobulin heavy chain polypeptide comprises, consists essentially of, or consists of a complementarity determining region 1 (CDR) amino acid sequence of SEQ ID NO: 12, a CDR2 amino acid sequence of SEQ ID NO: 13, and a CDR3 amino acid sequence of SEQ ID NO: 14, wherein optionally (a) residue 9 of SEQ ID NO: 12 is replaced with a different amino acid residue, (b) residue 8 and/or residue 9 of SEQ ID NO: 13 is replaced with a different amino acid residue, (c) residue 5 of SEQ ID NO: 14 is replaced with a different amino acid residue, or (d) any combination of (a)-(c). When the inventive immunoglobulin heavy chain polypeptide consists essentially of a CDR1 amino acid sequence of SEQ ID NO: 12, a CDR2 amino acid sequence of SEQ ID NO: 13, and a CDR3 amino acid sequence of SEQ ID NO: 14 and optional amino acid replacements, additional components can be included in the polypeptide that do not materially affect the polypeptide (e.g., protein moieties such as biotin that facilitate purification or isolation). When the inventive immunoglobulin heavy chain polypeptide consists of a CDR1 amino acid sequence of SEQ ID NO: 12, a CDR2 amino acid sequence of SEQ ID NO: 13, and a CDR3 amino acid sequence of SEQ ID NO: 14 and optional amino acid replacements, the polypeptide does not comprise any additional components (i.e., components that are not endogenous to the inventive immunoglobulin heavy chain polypeptide).

In one embodiment, the isolated immunoglobulin heavy chain polypeptide can comprise a CDR1 amino acid sequence of SEQ ID NO: 12, a CDR2 amino acid sequence of SEQ ID NO: 13, and a CDR3 amino acid sequence of SEQ ID NO: 14, except that (a) residue 9 of SEQ ID NO: 12 is replaced with a different amino acid residue, (b) residue 8 and/or residue 9 of SEQ ID NO: 13 is replaced with a different amino acid residue, (c) residue 5 of SEQ ID NO: 14 is replaced with a different amino acid residue, or (d) any combination of (a)-(c). For example, the isolated immunoglobulin heavy chain polypeptide can comprise a CDR1 amino acid sequence of SEQ ID NO: 12, a CDR2 amino acid sequence of SEQ ID NO: 13, and a CDR3 amino acid sequence of SEQ ID NO: 14, except that residue 9 of SEQ ID NO: 12 is replaced with a different amino acid residue, residue 8 of SEQ ID NO: 13, and residue 9 of SEQ ID NO: 13 is replaced with a different amino acid residue. Alternatively, the isolated immunoglobulin heavy chain polypeptide can comprise a CDR1 amino acid sequence of SEQ ID NO: 12, a CDR2 amino acid sequence of SEQ ID NO: 13, and a CDR3 amino acid sequence of SEQ ID NO: 14, except that residue 9 of SEQ ID NO: 12 is replaced with a different amino acid residue and residue 5 of SEQ ID NO: 14 is replaced with a different amino acid residue. In another embodiment, the isolated immunoglobulin heavy chain polypeptide can comprise a CDR1 amino acid sequence of SEQ ID NO: 12, a CDR2 amino acid sequence of SEQ ID NO: 13, and a CDR3 amino acid sequence of SEQ ID NO: 14, except that residue 9 of SEQ ID NO: 12 is replaced with a different amino acid residue, residue 8 of SEQ ID NO: 13 is replaced with a different amino acid residue, residue 9 of SEQ ID NO: 13 is replaced with a different amino acid residue, and residue 5 of SEQ ID NO: 14 is replaced with a different amino acid residue. Each of residue 9 of SEQ ID NO: 12, residues 8 and 9 of SEQ ID NO: 13, and residue 5 of SEQ ID NO: 14 can be replaced with any suitable amino acid residue that can be the same or different in each position. For example, the amino acid residue of a first position can be replaced with a first different amino acid residue, and the amino acid residue of a second position can be replaced with a second different amino acid residue, wherein the first and second different amino acid residues are the same or different. In one embodiment, the isolated immunoglobulin heavy chain polypeptide comprises a CDR1 amino acid sequence of SEQ ID NO: 12, a CDR2 amino acid sequence of SEQ ID NO: 13, and a CDR3 amino acid sequence of SEQ ID NO: 14, except that residue 9 of SEQ ID NO: 12 is replaced with a leucine (L) residue. In another embodiment, the isolated immunoglobulin heavy chain polypeptide comprises a CDR1 amino acid sequence of SEQ ID NO: 12, a CDR2 amino acid sequence of SEQ ID NO: 13, and a CDR3 amino acid sequence of SEQ ID NO: 14, except that (a) residue 8 of SEQ ID NO: 13 is replaced with a tyrosine (Y) residue, and/or (b) residue 9 of SEQ ID NO: 13 is replaced with an alanine (A) residue. In another embodiment, the isolated immunoglobulin heavy chain polypeptide comprises a CDR1 amino acid sequence of SEQ ID NO: 12, a CDR2 amino acid sequence of SEQ ID NO: 13, and a CDR3 amino acid sequence of SEQ ID NO: 14, except that residue 5 of SEQ ID NO: 14 is replaced with a threonine (T) residue.

Exemplary immunoglobulin heavy chain polypeptides as described above can comprise any one of the following amino acid sequences: SEQ ID NO: 15, SEQ ID NO: 16, SEQ ID NO: 17, or SEQ ID NO: 18.

The invention provides an isolated immunoglobulin heavy chain polypeptide comprises, consists essentially of, or consists of a complementarity determining region 1 (CDR) amino acid sequence of SEQ ID NO: 19, a CDR2 amino acid sequence of SEQ ID NO: 20, and a CDR3 amino acid sequence of SEQ ID NO: 21. When the inventive immunoglobulin heavy chain polypeptide consists essentially of a CDR1 amino acid sequence of SEQ ID NO: 19, a CDR2 amino acid sequence of SEQ ID NO: 20, and a CDR3 amino acid sequence of SEQ ID NO: 21, additional components can be included in the polypeptide that do not materially affect the polypeptide (e.g., protein moieties such as biotin that facilitate purification or isolation). When the inventive immunoglobulin heavy chain polypeptide consists of a CDR1 amino acid sequence of SEQ ID NO: 19, a CDR2 amino acid sequence of SEQ ID NO: 20, and a CDR3 amino acid sequence of SEQ ID NO: 21, the polypeptide does not comprise any additional components (i.e., components that are not endogenous to the inventive immunoglobulin heavy chain polypeptide). Exemplary immunoglobulin heavy chain polypeptides as described above can comprise any one of the following amino acid sequences: SEQ ID NO: 22, SEQ ID NO: 23, SEQ ID NO: 24, or SEQ ID NO: 25.

In addition, one or more amino acids can be inserted into the aforementioned immunoglobulin heavy chain polypeptides. Any number of any suitable amino acids can be inserted into the amino acid sequence of the immunoglobulin heavy chain polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy chain polypeptide. Preferably, 1-10 amino acids (e.g., 1, 2, 3, 4, 5, 6, 7, 8, 9, or 10 amino acids) are inserted into the amino acid sequence of the immunoglobulin heavy chain polypeptide. In this respect, the amino acid(s) can be inserted into any one of the aforementioned immunoglobulin heavy chain polypeptides in any suitable location. Preferably, the amino acid(s) are inserted into a CDR (e.g., CDR1, CDR2, or CDR3) of the immunoglobulin heavy chain polypeptide.

The invention provides an isolated immunoglobulin heavy chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NOs: 4-11, SEQ ID NOs: 15-18, and SEQ ID NOs: 22-25. Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

The invention provides an immunoglobulin light chain polypeptide that comprises a complementarity determining region 1 (CDR) amino acid sequence of SEQ ID NO: 26 and a CDR2 amino acid sequence of SEQ ID NO: 27. In one embodiment of the invention, the isolated immunoglobulin light chain polypeptide comprises, consists essentially of, or consists of a CDR1 amino acid sequence of SEQ ID NO: 26 and a CDR2 amino acid sequence of SEQ ID NO: 27. When the inventive immunoglobulin light chain polypeptide consists essentially of a CDR1 amino acid sequence of SEQ ID NO: 26 and a CDR2 amino acid sequence of SEQ ID NO: 27, additional components can be included in the polypeptide that do not materially affect the polypeptide (e.g., protein moieties such as biotin that facilitate purification or isolation). When the inventive immunoglobulin light chain polypeptide consists of a CDR1 amino acid sequence of SEQ ID NO: 26 and a CDR2 amino acid sequence of SEQ ID NO: 27, the polypeptide does not comprise any additional components (i.e., components that are not endogenous to the inventive immunoglobulin light chain polypeptide). Exemplary immunoglobulin light chain polypeptides as described above can comprise SEQ ID NO: 28 or SEQ ID NO: 29.

The invention provides an isolated immunoglobulin light chain polypeptide comprises a complementarity determining region 1 (CDR) amino acid sequence of SEQ ID NO: 30 and a CDR2 amino acid sequence of SEQ ID NO: 31. In one embodiment of the invention, the isolated immunoglobulin light chain polypeptide comprises, consists of, or consists essentially of a CDR1 amino acid sequence of SEQ ID NO: 30 and a CDR2 amino acid sequence of SEQ ID NO: 31, wherein optionally residue 12 of SEQ ID NO: 30 is replaced with a different amino acid residue. When the inventive immunoglobulin light chain polypeptide consists essentially of a CDR1 amino acid sequence of SEQ ID NO: 30 and a CDR2 amino acid sequence of SEQ ID NO: 31 and optional amino acid replacements, additional components can be included in the polypeptide that do not materially affect the polypeptide (e.g., protein moieties such as biotin that facilitate purification or isolation). When the inventive immunoglobulin light chain polypeptide consists of a CDR1 amino acid sequence of SEQ ID NO: 30 and a CDR2 amino acid sequence of SEQ ID NO: 31 and optional amino acid replacements, the polypeptide does not comprise any additional components (i.e., components that are not endogenous to the inventive immunoglobulin light chain polypeptide).

In this respect, for example, the isolated immunoglobulin light chain polypeptide can comprise a CDR1 amino acid sequence of SEQ ID NO: 30 and a CDR2 amino acid sequence of SEQ ID NO: 31, except that residue 12 of SEQ ID NO: 30 is replaced with a different amino acid residue. Residue 12 of SEQ ID NO: 30 can be replaced with any suitable amino acid residue. In one embodiment, the isolated immunoglobulin light chain polypeptide can comprise a CDR1 amino acid sequence of SEQ ID NO: 30 and a CDR2 amino acid sequence of SEQ ID NO: 31, except that residue 12 of SEQ ID NO: 30 is replaced with a threonine (T) residue. Exemplary immunoglobulin light chain polypeptides as described above can comprise any one of the following amino acid sequences: SEQ ID NO: 32, SEQ ID NO: 33, or SEQ ID NO: 34.

The invention provides an isolated immunoglobulin light chain polypeptide comprises a complementarity determining region 1 (CDR) amino acid sequence of SEQ ID NO: 35, a CDR2 amino acid sequence of SEQ ID NO: 36, and a CDR3 amino acid sequence of SEQ ID NO: 37. In one embodiment, the immunoglobulin light chain polypeptide comprises, consists essentially of, or consists of a CDR1 amino acid sequence of SEQ ID NO: 35, a CDR2 amino acid sequence of SEQ ID NO: 36, and a CDR3 amino acid sequence of SEQ ID NO: 37, wherein optionally (a) residue 5 of SEQ ID NO: 36 is replaced with a different amino acid residue, and/or (b) residue 4 of SEQ ID NO: 37 is replaced with a different amino acid residue. When the inventive immunoglobulin light chain polypeptide consists essentially of a CDR1 amino acid sequence of SEQ ID NO: 35, a CDR2 amino acid sequence of SEQ ID NO: 36, and a CDR3 amino acid sequence of SEQ ID NO: 37 and optional amino acid replacements, additional components can be included in the polypeptide that do not materially affect the polypeptide (e.g., protein moieties such as biotin that facilitate purification or isolation). When the inventive immunoglobulin light chain polypeptide consists of a CDR1 amino acid sequence of SEQ ID NO: 35, a CDR2 amino acid sequence of SEQ ID NO: 36, and a CDR3 amino acid sequence of SEQ ID NO: 37 and optional amino acid replacements, the polypeptide does not comprise any additional components (i.e., components that are not endogenous to the inventive immunoglobulin light chain polypeptide). In this respect, for example, the isolated immunoglobulin light chain polypeptide can comprise a CDR1 amino acid sequence of SEQ ID NO: 35, a CDR2 amino acid sequence of SEQ ID NO: 36, and a CDR3 amino acid sequence of SEQ ID NO: 37. Alternatively, the isolated immunoglobulin light chain polypeptide can comprise a CDR1 amino acid sequence of SEQ ID NO: 35, a CDR2 amino acid sequence of SEQ ID NO: 36, and a CDR3 amino acid sequence of SEQ ID NO: 37, except that (a) residue 5 of SEQ ID NO: 36 is replaced with a different amino acid residue, and/or (b) residue 4 of SEQ ID NO: 37 is replaced with a different amino acid residue.

Each of residue 5 of SEQ ID NO: 36 and residue 4 of SEQ ID NO: 37 can be replaced with any suitable amino acid residue that can be the same or different in each position. For example, the amino acid residue of a first position can be replaced with a first different amino acid residue, and the amino acid residue of a second position can be replaced with a second different amino acid residue, wherein the first and second different amino acid residues are the same or different.

In one embodiment, the isolated immunoglobulin light chain polypeptide comprises a CDR1 amino acid sequence of SEQ ID NO: 35, a CDR2 amino acid sequence of SEQ ID NO: 36, and a CDR3 amino acid sequence of SEQ ID NO: 37, except that (a) residue 5 of SEQ ID NO: 36 is replaced with a leucine (L) residue, and/or (b) residue 4 of SEQ ID NO: 37 is replaced with an asparagine (N) residue. Exemplary immunoglobulin light chain polypeptides as described above can comprise any one of the following amino acid sequences: SEQ ID NO: 38, SEQ ID NO: 39, SEQ ID NO: 40, or SEQ ID NO: 41.

In addition, one or more amino acids can be inserted into the aforementioned immunoglobulin light chain polypeptides. Any number of any suitable amino acids can be inserted into the amino acid sequence of the immunoglobulin light chain polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin light chain polypeptide. Preferably, 1-10 amino acids (e.g., 1, 2, 3, 4, 5, 6, 7, 8, 9, or 10 amino acids) are inserted in to the amino acid sequence of the immunoglobulin light chain polypeptide. In this respect, the amino acid(s) can be inserted into any one of the aforementioned immunoglobulin light chain polypeptides in any suitable location. Preferably, the amino acid(s) are inserted into a CDR (e.g., CDR1, CDR2, or CDR3) of the immunoglobulin light chain polypeptide.

The invention provides an isolated immunoglobulin light chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NO: 28, SEQ ID NO: 29, SEQ ID NO: 32, SEQ ID NO: 33, SEQ ID NO: 34, SEQ ID NO: 38, SEQ ID NO: 39, SEQ ID NO: 40, and SEQ ID NO: 41. Nucleic acid or amino acid sequence "identity," as described herein, can be determined using the methods described herein.

The invention provides an isolated programmed death 1 (PD-1)-binding agent comprising, consisting essentially of, or consisting of the inventive isolated amino acid sequences described herein. By "programmed death 1 (PD-1)-binding agent" is meant a molecule, preferably a proteinaceous molecule, that binds specifically to the programmed death 1 protein (PD-1). Preferably, the PD-1-binding agent is an antibody or a fragment (e.g., immunogenic fragment) thereof. The isolated PD-1-binding agent of the invention comprises, consists essentially of, or consists of the inventive isolated immunoglobulin heavy chain polypeptide and/or the inventive isolated immunoglobulin light chain polypeptide. In one embodiment, the isolated PD-1-binding agent comprises, consists essentially of, or consists of the inventive immunoglobulin heavy chain polypeptide or the inventive immunoglobulin light chain polypeptide. In another embodiment, the isolated PD-1-binding agent comprises, consists essentially of, or consists of the inventive immunoglobulin heavy chain polypeptide and the inventive immunoglobulin light chain polypeptide.

The invention is not limited to an isolated PD-1-binding agent that comprises, consists essentially of, or consists of an immunoglobulin heavy chain polypeptide and/or light chain polypeptide having replacements, insertions, and/or deletions of the specific amino acid residues disclosed herein. Indeed, any amino acid residue of the inventive immunoglobulin heavy chain polypeptide and/or the inventive immunoglobulin light chain polypeptide can be replaced, in any combination, with a different amino acid residue, or can be deleted or inserted, so long as the biological activity of the PD-1-binding agent is enhanced or improved as a result of the amino acid replacements, insertions, and/or deletions. The "biological activity" of an PD-1-binding agent refers to, for example, binding affinity for PD-1 or a particular PD-1 epitope, neutralization or inhibition of PD-1 protein binding to its ligands PD-L1 and PD-L1, neutralization or inhibition of PD-1 protein activity in vivo (e.g., $IC_{50}$), pharmacokinetics, and cross-reactivity (e.g., with non-human homologs or orthologs of the PD-1 protein, or with other proteins or tissues). Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

The terms "inhibit" or "neutralize," as used herein with respect to the activity of a PD-1-binding agent, refer to the ability to substantially antagonize, prohibit, prevent, restrain, slow, disrupt, alter, eliminate, stop, or reverse the progression or severity of, for example, the biological activity of a PD-1 protein, or a disease or condition associated with an PD-1 protein. The isolated PD-1-binding agent of the invention preferably inhibits or neutralizes the activity of a PD-1 protein by at least about 20%, about 30%, about 40%, about 50%, about 60%, about 70%, about 80%, about 90%, about 95%, about 100%, or a range defined by any two of the foregoing values.

The isolated PD-1-binding agent of the invention can be a whole antibody, as described herein, or an antibody fragment. The terms "fragment of an antibody," "antibody fragment," and "functional fragment of an antibody" are used interchangeably herein to mean one or more fragments of an antibody that retain the ability to specifically bind to an antigen (see, generally, Holliger et al., Nat. Biotech., 23(9): 1126-1129 (2005)). The isolated PD-1 binding agent can contain any PD-1-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $CH_1$ domains, (ii) a $F(ab')_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an $F(ab')_2$ fragment using mild reducing conditions, (v) a disulfide-stabilized Fv fragment (dsFv), and (vi) a domain antibody (dAb), which is an antibody single variable region domain (VH or VL) polypeptide that specifically binds antigen.

In embodiments where the isolated PD-1-binding agent comprises a fragment of the immunoglobulin heavy chain or light chain polypeptide, the fragment can be of any size so long as the fragment binds to, and preferably inhibits the activity of, a PD-1 protein. In this respect, a fragment of the immunoglobulin heavy chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids. Similarly, a fragment of the immunoglobulin light chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids.

When the PD-1-binding agent is an antibody or antibody fragment, the antibody or antibody fragment desirably comprises a heavy chain constant region ($F_c$) of any suitable class. Preferably, the antibody or antibody fragment comprises a heavy chain constant region that is based upon wild-type IgG1, IgG2, or IgG4 antibodies, or variants thereof.

The PD-1-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024 A1.

The isolated PD-1-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The isolated PD-1-binding agent also can be an antibody conjugate. In this respect, the isolated PD-1-binding agent can be a conjugate of (1) an antibody, an alternative scaffold, or fragments thereof, and (2) a protein or non-protein moiety comprising the PD-1-binding agent. For example, the PD-1-binding agent can be all or part of an antibody conjugated to a peptide, a fluorescent molecule, or a chemotherapeutic agent.

The isolated PD-1-binding agent can be, or can be obtained from, a human antibody, a non-human antibody, or a chimeric antibody. By "chimeric" is meant an antibody or fragment thereof comprising both human and non-human regions. Preferably, the isolated PD-1-binding agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. In a preferred embodiment of the invention, CDRH3 of the inventive PD-1-binding agent is obtained or derived from a mouse monoclonal antibody, while the remaining variable regions and constant region of the inventive PD-1-binding agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology*, 5th Ed., Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, N.J. (2009)), including, e.g., grafting of non-human CDRs onto a human antibody scaffold (see, e.g., Kashmiri et al., *Methods*, 36(1): 25-34 (2005); and Hou et al., *J. Biochem.*, 144(1): 115-120 (2008)). In one embodiment, a humanized antibody can be produced using the methods described in, e.g., U.S. Patent Application Publication 2011/0287485 A1.

In a preferred embodiment, the PD-1-binding agent binds an epitope of a PD-1 protein which blocks the binding of PD-1 to PD-L1. The invention also provides an isolated or purified epitope of a PD-1 protein which blocks the binding of PD-1 to PD-L1 in an indirect or allosteric manner.

The invention also provides one or more isolated or purified nucleic acid sequences that encode the inventive immunoglobulin heavy chain polypeptide, the inventive immunoglobulin light chain polypeptide, and the inventive PD-1-binding agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like). Nucleic acid sequences encoding the inventive immunoglobulin heavy chain polypeptides include, for example, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55. Nucleic acid sequences encoding the inventive immunoglobulin light chain polypeptides include, for example, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, and SEQ ID NO: 64.

The invention further provides a vector comprising one or more nucleic acid sequences encoding the inventive immunoglobulin heavy chain polypeptide, the inventive immunoglobulin light chain polypeptide, and/or the inventive PD-1-binding agent. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the inventive immunoglobulin heavy polypeptide, the inventive immunoglobulin light chain polypeptide, and/or the inventive PD-1-binding agent, the vector preferably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ system (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colbere-Garapin et al., *J. Mol. Biol.*, 150: 1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad. Sci. USA*, 48: 2026-2034 (1962); Lowy et al., *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), UCOE from Millipore (Billerica, Mass.), and pCI or pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

Nucleic acid sequences encoding the inventive amino acid sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding the inventive amino acid sequences can be introduced into a host cell that is capable of expressing the polypeptides encoded thereby, including any suitable prokaryotic or eukaryotic cell. As such, the invention provides an isolated cell comprising the inventive vector. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas*, *Streptomyces*, *Salmonella*, and *Enwinia*. Particularly useful prokaryotic cells include the various strains of *Escherichia coli* (e.g., K12, HB101 (ATCC No. 33694), DH5α, DH10, MC1061 (ATCC No. 53338), and CC102).

Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia, Rhino-sporidium, Saccharomyces*, and *Schizosaccharomyces*. Preferred yeast cells include, for example, *Saccharomyces cerivisae* and *Pichia pastoris*.

Suitable insect cells are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and HIS (Invitrogen, Carlsbad, Calif.).

Preferably, mammalian cells are utilized in the invention. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

Most preferably, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al., *Proc. Natl. Acad. Sci. USA*, 85: 1581-1585 (1988)), Raji cells (CCL-86), and derivatives thereof.

A nucleic acid sequence encoding the inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)). Phage or viral vectors can be introduced into host cells, after growth of infectious particles in suitable packaging cells, many of which are commercially available.

The invention provides a composition comprising an effective amount of the inventive immunoglobulin heavy chain polypeptide, the inventive immunoglobulin light chain polypeptide, the inventive PD-1-binding agent, the inventive nucleic acid sequence encoding any of the foregoing, or the inventive vector comprising the inventive nucleic acid sequence. Preferably, the composition is a pharmaceutically acceptable (e.g., physiologically acceptable) composition, which comprises a carrier, preferably a pharmaceutically acceptable (e.g., physiologically acceptable) carrier, and the inventive amino acid sequences, antigen-binding agent, or vector. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy, 21st Edition*, Lippincott Williams & Wilkins, Philadelphia, Pa. (2001).

The invention further provides a method of treating any disease or disorder in which the improper expression (e.g., overexpression) or increased activity of a PD-1 protein causes or contributes to the pathological effects of the disease, or a decrease in PD-1 protein levels or activity has a therapeutic benefit in mammals, preferably humans. The invention also provides a method of treating a cancer or an infectious disease in a mammal. The method comprises administering the aforementioned composition to a mammal having a cancer or an infectious disease, whereupon the cancer or infectious disease is treated in the mammal. As discussed herein, PD-1 is abnormally expressed in a variety of cancers (see, e.g., Brown et al., *J. Immunol.*, 170: 1257-1266 (2003); and Flies et. al., *Yale Journal of Biology and Medicine*, 84: 409-421 (2011)), and PD-L1 expression in some renal cell carcinoma patients correlates with tumor aggressiveness. The inventive method can be used to treat any type of cancer known in the art, such as, for example, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma (see, e.g., Bhatia et al., *Curr. Oncol. Rep.*, 13(6): 488-497 (2011)). The inventive method can be used to treat any type of infectious disease (i.e., a disease or disorder caused by a bacterium, a virus, a fungus, or a parasite). Examples of infectious diseases that can be treated by the inventive method include, but are not limited to, diseases caused by a human immunodeficiency virus (HIV), a respiratory syncytial virus (RSV), an influenza virus, a dengue virus, a hepatitis B virus (HBV, or a hepatitis C virus (HCV)). Administration of a composition comprising the inventive immunoglobulin heavy chain polypeptide, the inventive immunoglobulin light chain polypeptide, the inventive PD-1-binding agent, the inventive nucleic acid sequence encoding any of the foregoing, or the inventive vector comprising the inventive nucleic acid sequence induces an immune response against a cancer or infectious disease in a mammal. An "immune response" can entail, for example, antibody production and/or the activation of immune effector cells (e.g., T-cells).

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the PD-1-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the PD-1-binding agent to elicit a desired response in the individual. For example, a therapeutically effective amount of a PD-1-binding agent of the invention is an amount which decreases PD-1 protein bioactivity in a human and/or enhances the immune response against a cancer or infectious disease.

Alternatively, the pharmacologic and/or physiologic effect may be prophylactic, i.e., the effect completely or partially prevents a disease or symptom thereof. In this respect, the inventive method comprises administering a "prophylactically effective amount" of the PD-1-binding agent. A "prophylactically effective amount" refers to an amount effective, at dosages and for periods of time necessary, to achieve a desired prophylactic result (e.g., prevention of disease onset).

A typical dose can be, for example, in the range of 1 pg/kg to 20 mg/kg of animal or human body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values), preferably from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising an effective amount of the inventive immunoglobulin heavy chain polypeptide, the inventive immunoglobulin light chain polypeptide, the inventive PD-1-binding agent, the inventive nucleic acid sequence encoding any of the foregoing, or the inventive vector comprising the inventive nucleic acid sequence can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive PD-1-binding agent can be measured by any suitable method known in the art. For example, the biological activity can be assessed by determining the stability of a particular PD-1-binding agent. In one embodiment of the invention, the PD-1-binding agent (e.g., an antibody) has an in vivo half life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the PD-1-binding agent has an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the PD-1-binding agent has an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The biological activity of a particular PD-1-binding agent also can be assessed by determining its binding affinity to a PD-1 protein or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 100 micromolar (µM) (e.g., from about 1 picomolar (pM) to about 1 nanomolar (nM), from about 1 nM to about 1 micromolar (04), or from about 1 µM to about 100 µM). In one embodiment, the PD-1-binding agent can bind to an PD-1 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the PD-1-binding agent can bind to PD-1 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA (see, e.g., Janeway et al. (eds.), *Immunobiology*, 5th ed., Garland Publishing, New York, N.Y., 2001).

The PD-1-binding agent of the invention may be administered alone or in combination with other drugs (e.g., as an adjuvant). For example, the PD-1-binding agent can be administered in combination with other agents for the treatment or prevention of the diseases disclosed herein. In this respect, the PD-1-binding agent can be used in combination with at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery. When the inventive method treats an infectious disease, the PD-1-binding agent can be administered in combination with at least one anti-bacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

In another embodiment, the inventive PD-1 binding agent can be administered in combination with other agents that inhibit immune checkpoint pathways. For example, the inventive PD-1 binding agent can be administered in combination with agents that inhibit or antagonize the CTLA-4, TIM-3 or LAG-3 pathways. Combination treatments that simultaneously target two or more of these immune checkpoint pathways have demonstrated improved and potentially synergistic antitumor activity (see, e.g., Sakuishi et al., *J. Exp. Med.*, 207: 2187-2194 (2010); Ngiow et al., *Cancer Res.*, 71: 3540-3551 (2011); and Woo et al., *Cancer Res.*, 72: 917-927 (2012)). In one embodiment, the inventive PD-1 binding agent is administered in combination with an antibody that binds to TIM-3 and/or an antibody that binds to LAG-3. In this respect, the inventive method of treating a cancer or an infectious disease in a mammal can further comprise administering to the mammal a composition comprising (i) an antibody that binds to a TIM-3 protein and (ii) a pharmaceutically acceptable carrier or a composition comprising (i) an antibody that binds to a LAG-3 protein and (ii) a pharmaceutically acceptable carrier.

In addition to therapeutic uses, the PD-1-binding agent described herein can be used in diagnostic or research applications. In this respect, the PD-1-binding agent can be used in a method to diagnose a cancer or infectious disease. In a similar manner, the PD-1-binding agent can be used in an assay to monitor PD-1 protein levels in a subject being tested for a disease or disorder that is associated with abnormal PD-1 expression. Research applications include, for example, methods that utilize the PD-1-binding agent and a label to detect a PD-1 protein in a sample, e.g., in a human body fluid or in a cell or tissue extract. The PD-1-binding agent can be used with or without modification, such as covalent or non-covalent labeling with a detectable moiety. For example, the detectable moiety can be a radioisotope (e.g., $^3$H, $^{14}$C, $^{32}$P, $^{35}$S, or $^{125}$I), a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., *Nature*, 194: 495-496 (1962); David et al., *Biochemistry*, 13: 1014-1021 (1974); Pain et al., *J. Immunol. Meth.*, 40: 219-230 (1981); and Nygren, *J. Histochem. and Cytochem.*, 30: 407-412 (1982)).

PD-1 protein levels can be measured using the inventive PD-1-binding agent by any suitable method known in the art. Such methods include, for example, radioimmunoassay (MA), and FACS. Normal or standard expression values of PD-1 protein can be established using any suitable technique, e.g., by combining a sample comprising, or suspected of comprising, a PD-1 polypeptide with a PD-1-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of PD-1 polypeptide expressed in a sample is then compared with a standard value.

The PD-1-binding agent can be provided in a kit, i.e., a packaged combination of reagents in predetermined amounts with instructions for performing a diagnostic assay. If the PD-1-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the invention but, of course, should not be construed as in any way limiting its scope.

Example 1

This example demonstrates a method of generating monoclonal antibodies directed against human PD-1.

Several forms of genes encoding human PD-1 and its ligands PD-L1 and PD-L2 were generated as antigens for use in mouse immunization, hybridoma screening, and affinity maturation of CDR-grafted antibodies, and are schematically depicted in FIG. 1. Full-length human and cynomolgus monkey PD-1 genes were expressed with their native leader sequence and no added tags using a ubiquitous chromatin opening element (UCOE) single expression vector with hygromycin selection (Millipore, Billerica, Mass.). CHO-K1 cells were stably transfected with Lipofectamine LTX (Life Technologies, Carlsbad, Calif.) according to the manufacturer's instructions. Following selection with hygromycin, cells expressing PD-1 on the cell surface were identified by flow cytometry using a PE-conjugated mouse antibody to human PD-1 (BD Bioscience, Franklin Lakes, N.J.) and subcloned. Subclones were then selected for high-level and uniform PD-1 expression.

Nucleic acid sequences encoding soluble monomeric forms of the extracellular domain (ECD) of human and cynomolgus monkey PD-1 were constructed with His tags appended to the C-terminus of the ECD or as soluble dimeric fusion proteins with mouse IgG2a Fc as indicated in FIG. 1. Nucleic acid sequences encoding soluble dimeric forms of the ECDs of human PD-L1 and PD-L2 were constructed as fusion proteins with mouse IgG1 Fc as indicated in FIG. 1. Soluble proteins were expressed transiently in HEK 293 cells or in stable CHO cell lines using standard techniques. His-tagged proteins were purified from cell culture supernatant via Ni-affinity column chromatography followed by size exclusion chromatography. IgG-Fc fusion proteins were purified using protein A/G affinity chromatography. Purified proteins were analyzed by SDS-PAGE and size-exclusion chromatography to ensure homogeneity. Additionally, identity and size were confirmed by mass spectrometry.

For FACS sorting experiments, purified proteins were labeled with biotin using an NHS ester crosslinker (Thermo-Fisher Scientific, Inc., Waltham, Mass.) or the fluorescent dye DyLight 650 (Thermo-Fisher Scientific, Inc., Waltham, Mass.) using standard techniques.

Mice were immunized with either CHO cells expressing full-length PD-1 on the cell surface or the PD-1 ECD His protein. Specifically, female BALB/c mice (7 weeks old) were purchased from Harlan Laboratories, Inc. (Indianapolis, Ind.) and divided into two groups. After six days of acclimatization, one group of animals was immunized with four weekly doses of purified human PD-1 ECD-His at 50 µg/mouse, as a 1:1 emulsion with TITERMAX GOLD™ (Sigma Aldrich, St. Louis, Mo.). Immunization was carried out subcutaneously around the armpits and inguinal regions. The second group of animals was injected with four weekly doses of CHO-K1 cells stably expressing full length human PD-1 ($5 \times 10^6$ cells/mouse) subcutaneously around the inguinal regions. After ten days, animals were bled for measurement of the serum titer to PD-1, and one animal from each group was boosted with soluble human PD-1 after a 3-week rest. After three days, spleens, axillary/brachial lymph nodes, and inguinal lymph nodes were collected from each animal. Single cell suspensions of cells from all tissues collected from both animals were pooled and used for generation of hybridomas by cell fusion using standard techniques. Two different myeloma cell lines were used for fusion, FO (as described in de St. Groth and Scheidegger, *J.*

*Immunol. Methods,* 35: 1-21 (1980)) and P3X63Ag8.653 (as described in Kearney et al., *J. Immunol.,* 123: 1548-1550 (1979)).

Hybridoma supernatants from ten 96-well plates were screened for binding to a CHO-K1 cell clone stably transfected with a nucleic acid sequence encoding full length human PD-1 and compared to binding to untransfected CHO-K1 cells. Specifically, hybridoma supernatants were diluted 1:1 with PBS/2% FBS and incubated with an equal volume of PD-1 CHO-K1 cells ($2.5 \times 10^5$ cells in PBS, 2% FBS) for 30 minutes at 4° C. Cells were centrifuged, washed once with PBS/1% FBS, and incubated with APC-conjugated goat anti-mouse IgG (H+L) (Southern Biotechnology, Birmingham, Ala.) for 30 minutes at 4° C. Cells were washed twice in PBS/2% FBS, resuspended in PBS, 2% FBS, 1% paraformaldehyde, and fluorescence analyzed on a BD FACSARRAY™ Bioanalyzer (BD Biosciences, Franklin Lakes, N.J.). Mouse IgG levels were quantified by ELISA.

Based on strong binding to PD-1 CHO cells, 46 parental wells were expanded, and the supernatants were tested for the ability to block binding of DyL650-labeled PD-L1-mIgG1 Fc fusion protein to PD-1 CHO cells. Specifically, purified mouse monoclonal antibodies were incubated in a dose response with the $E_{C30}$ concentration of PD-L1-DyL650 (10 nM), and inhibition was quantified by flow cytometry. Cells from wells showing the best PD-L1 blocking activity and highest levels of mouse IgG were subcloned for further analysis, including purification and heavy and light chain ($V_H$ and $V_L$) sequencing. Eleven of the strongest blockers of PD-1/PD-L1 interaction were selected for subcloning. Following re-confirmation of PD-1 binding and PD-L1 blocking, selected subclones were scaled up, and supernatant was submitted for antibody purification. Purified antibodies were verified for binding to both human and cynomolgus monkey PD-1 and for PD-L1 blocking activity. $K_D$ values were determined by surface plasmon resonance on a BIACORE™ T200 instrument (GE Healthcare, Waukesha, Wis.), and kinetic constants were determined using the BIACORE™ T200 evaluation software (GE Healthcare, Waukesha, Wis.). In this respect, antibodies were captured on a BIACORE™ CM5 chip to which GE anti-mouse IgG was coupled. PD-1-His monomer was flowed over the captured antibody using two- or three-fold serial dilutions beginning with 500 nM at the highest concentration. The resulting sensorgrams were fit globally using a 1:1 binding model to calculate on- and off-rates and the subsequent affinities ($K_D$).

The results of this example demonstrate a method of producing monoclonal antibodies that bind to human and cynomolgus monkey PD-1 and block PD-1 ligand binding.

Example 2

This example describes the design and generation of CDR-grafted and chimeric anti-PD-1 monoclonal antibodies.

Subclones of the hybridomas which produced PD-1-binding antibodies with PD-L1 blocking activity as described in Example 1 were isotyped, subjected to RT-PCR for cloning the antibody heavy chain variable region ($V_H$) and light chain variable region ($V_L$), and sequenced. Specifically, RNA was isolated from cell pellets of hybridoma clones ($5 \times 10^5$ cells/pellet) using the RNEASY™ kit (Qiagen, Venlo, Netherlands), and cDNA was prepared using oligo-dT-primed SUPERSCRIPT™ III First-Strand Synthesis System (Life Technologies, Carlsbad, Calif.). PCR amplification of the $V_L$ utilized a pool of 9 or 11 degenerate mouse $V_L$ forward primers (see Kontermann and Dubel, eds., Antibody Engineering, Springer-Verlag, Berlin (2001)) and a mouse κ constant region reverse primer. PCR amplification of the $V_H$ utilized a pool of 12 degenerate mouse $V_H$ forward primers (Kontermann and Dubel, supra) and a mouse γ1 or γ2a constant region reverse primer (based on isotyping of purified antibody from each clone) with the protocol recommended in the SUPERSCRIPT™ III First-Stand Synthesis System (Life Technologies, Carlsbad, Calif.). PCR products were purified and cloned into pcDNA3.3-TOPO (Life Technologies, Carlsbad, Calif.). Individual colonies from each cell pellet (24 heavy chains and 48 light chains) were selected and sequenced using standard Sanger sequencing methodology (Genewiz, Inc., South Plainfield, N.J.). Variable region sequences were examined and aligned with the closest human heavy chain or light chain V-region germline sequence. Three antibodies were selected for CDR-grafting: (1) 9A2, comprising a $V_H$ of SEQ ID NO: 4 and a $V_L$ of SEQ ID NO: 28, (2) 10B11, comprising a $V_H$ of SEQ ID NO: 15 and a $V_L$ of SEQ ID NO: 32, and (3) 6E9, comprising a $V_H$ of SEQ ID NO: 22 and a $V_L$ of SEQ ID NO: 38.

CDR-grafted antibody sequences were designed by grafting CDR residues from each of the above-described mouse antibodies into the closest human germline homologue. CDR-grafted antibody variable regions were synthesized and expressed with human IgG1/κ constant regions for analysis. In addition, mouse:human chimeric antibodies were constructed using the variable regions of the above-described mouse antibodies linked to human IgG1/κ constant regions. Chimeric and CDR-grafted antibodies were characterized for binding to human and cynomolgus monkey PD-1 antigens and for activity in the PD-1/PD-L1 blocking assay as described above.

The functional antagonist activity of chimeric and CDR-grafted antibodies also was tested in a human $CD4^+$ T-cell mixed lymphocyte reaction (MLR) assay in which activation of CD4+ T-cells in the presence of anti-PD-1 antibodies is assessed by measuring IL-2 secretion. Because PD-1 is a negative regulator of T-cell function, antagonism of PD-1 was expected to result in increased T-cell activation as measured by increased IL-2 production. The 9A2, 10B11, and 6E9 CDR-grafted antibodies demonstrated antagonistic activity and were selected for affinity maturation.

The results of this example demonstrate a method of generating chimeric and CDR-grafted monoclonal antibodies that specifically bind to and inhibit PD-1.

Example 3

This example demonstrates affinity maturation of monoclonal antibodies directed against PD-1.

CDR-grafted antibodies derived from the original murine monoclonal antibodies, (9A2, 10B11, and 6E9) were subjected to affinity maturation via in vitro somatic hypermutation. Each antibody was displayed on the surface of HEK 293c18 cells using the SHM-XEL deciduous system (see Bowers et al., *Proc. Natl. Acad. Sci. USA,* 108: 20455-20460 (2011); and U.S. Patent Application Publication No. 2013/0035472). After establishment of stable episomal lines, a vector for expression of activation-induced cytosine deaminase (AID) was transfected into the cells to initiate somatic hypermutation as described in Bowers et al., supra. After multiple rounds of FACS sorting under conditions of increasing antigen binding stringency, a number of mutations in the variable region of each antibody were identified and recombined to produce mature humanized antibodies with improved properties.

A panel of six affinity-matured humanized heavy and light chain variable region sequences were paired (denoted APE1922, APE1923, APE1924, APE1950, APE1963 and APE2058) and selected for characterization, and are set forth in Table 1. The PD-1 binding properties of each of these antibody sequences were assayed using surface plasmon resonance (SPR) and solution-based affinity analysis. Antibodies were expressed from HEK 293 cells as human IgG1 antibodies and compared to the reference antibody, a human IgG1 version of BMS-936558, designated BMS.

SPR analyses were carried out using a BIACORE™ T200 instrument, and kinetic constants were determined using the BIACORE™ T200 evaluation software. Experimental parameters were chosen to ensure that saturation would be reached at the highest antigen concentrations and that Rmax values would be kept under 30 RU. GE anti-Human IgG (Fc-specific, approximately 7,000 RU) was immobilized on a BIACORE™ CM5 chip using EDC-activated amine coupling chemistry. Antibodies (0.5 μg/mL, 60 second capture time) were then captured using this surface. Next, monomeric soluble human PD1-Avi-His was flowed over captured antibody (300 second association, 300 second dissociation) using a three-fold serial dilution series from 500 nM to 2 nM. Captured antibody and antigen were removed between each cycle using 3 M $MgCl_2$ (60 second contact time) in order to ensure a fresh binding surface for each concentration of antigen. The resulting sensorgrams were fit globally using a 1:1 binding model in order to calculate on- and off-rates ($k_a$ and $k_d$, respectively), as well as affinities ($K_D$).

Solution-based affinity analyses were carried out using a KINEXA™ 3000 assay (Sapidyne Instruments, Boise, Idaho), and results were analyzed using KINEXA™ Pro Software 3.2.6. Experimental parameters were selected to reach a maximum signal with antibody alone between 0.8 and 1.2 V, while limiting nonspecific binding signal with buffer alone to less than 10% of the maximum signal. Azlactone beads (50 mg) were coated with antigen by diluting in a solution of PD-1-Avi-His (50 μg/mL in 1 mL) in 50 mM $Na_2CO_3$. The solution was rotated at room temperature for 2 hours, and beads were pelleted in a picofuge and washed twice with blocking solution (10 mg/mL BSA, 1 M Tris-HCl, pH 8.0). Beads were resuspended in blocking solution (1 mL), rotated at room temperature for 1 hour, and diluted in 25 volumes PBS/0.02% $NaN_3$. For affinity measurement, the secondary antibody was ALEXFLUOR™ 647 dye-anti-human IgG (500 ng/mL). Sample antibody concentrations were held constant (50 pM or 75 pM), while antigen PD1-Avi-His was titrated using a three-fold dilutions series from 1 μM to 17 pM. All samples were diluted in PBS, 0.2% $NaN_3$, 1 mg/mL BSA and allowed to equilibrate at room temperature for 30 hours. Additionally, samples containing only antibody and only buffer were tested in order to determine maximum signal and nonspecific binding signal, respectively. The results of the affinity analyses are set forth in Table 1. All of the selected antibodies exhibited higher affinities for PD-1 than the BMS reference antibody, with the highest affinity antibody being APE2058.

TABLE 1

| Antibody | $V_H$ SEQ ID NO: | $V_L$ SEQ ID NO: | BIACORE™ $k_a$ $(Ms)^{-1}$ | BIACORE™ $k_d$ $(s^{-1})$ | BIACORE™ $K_D$ (nM) | KINEXA™ $K_D$ (nM) |
|---|---|---|---|---|---|---|
| BMS | n/a | n/a | $8.8 \times 10^4$ | $2.1 \times 10^{-3}$ | 23 | 2 |
| APE1922 | 6 | 29 | $1.3 \times 10^5$ | $1.8 \times 10^{-3}$ | 15 | — |
| APE1923 | 7 | 29 | $1.9 \times 10^5$ | $1.7 \times 10^{-3}$ | 9 | 1 |
| APE1924 | 8 | 29 | $1.8 \times 10^5$ | $1.8 \times 10^{-3}$ | 10 | −1 |
| APE1950 | 9 | 29 | $1.5 \times 10^5$ | $2.5 \times 10^{-3}$ | 17 | — |
| APE1963 | 10 | 29 | $5.8 \times 10^4$ | $1.0 \times 10^{-3}$ | 17 | — |
| APE2058 | 23 | 40 | $3.0 \times 10^5$ | $6.4 \times 10^{-4}$ | 2 | 0.2 |

To assess binding of the antibodies to cell surface PD-1, binding to CHO cells expressing either human or cnyomolgus monkey PD-1 was determined by flow cytometry analysis as described above. In addition, blocking of the PD-1/PD-L1 interaction was assessed using DyL650 labeled PD-L1 (mouse IgG1 Fc fusion protein) and PD-1-expressing CHO cells as described above. High binding affinities for cell-surface PD-1 were observed for all tested affinity-matured antibody sequences, with reactivity to cynomolgus monkey PD-1 within a factor of 3-4 fold of human. Blocking of the PD-1/PD-L1 interaction was also efficient with all of the tested affinity-matured antibody sequences, with ICso values in the low nM range. These results were consistent with binding affinities assayed both by the BIACORE™ and KINEXA™ systems as well as cell surface $EC_{50}$ values.

Thermal stability of the selected antibodies was assessed using a Thermofluor assay as described in McConnell et al., *Protein Eng. Des. Sel.*, 26: 151 (2013). This assay assesses stability through the ability of a hydrophobic fluorescent dye to bind to hydrophobic patches on the protein surface which are exposed as the protein unfolds. The temperature at which 50% of the protein unfolds is determined (Tm) to measure thermal stability. This assay demonstrated that all of the tested affinity-matured antibody sequences had high thermal stability, and all were more stable than the reference antibody. APE2058 was the most stable antibody, exhibiting a Tm more than 10° C. greater than the Tm of the IgG1 version of BMS-936558.

De-risking of potential issues related to in vivo pharmokinetics of the tested antibodies was undertaken through (a) assessment of non-specific binding to target negative cells (see, e.g., Hotzel et al., *mAbs*, 4: 753-760 (2012)) and (b) measurement of differential neonatal Fc receptor (FcRn) dissociation properties (see, e.g., Wang et al., *Drug Metab. Disp.*, 39: 1469-1477 (2011)). To assess non-specific binding, antibodies were tested for binding to HEK 293f cells using a flow cytometry-based assay. The tested antibodies were compared to two FDA-approved antibodies, infliximab and denosumab. The results indicated that non-specific binding was low for all of the antibodies. To assess FcRn binding and dissociation, both human FcRn and cynomolgus FcRn were tested in a BIACORE™-based assay. Antibodies were bound to FcRn at pH 6.0, and after pH adjustment to 7.4, residual bound antibody was determined. The results of this assay are shown in Table 2.

TABLE 2

| Antibody | % Residual Binding at pH 7.4 | |
|---|---|---|
| | Human FcRn | Cyno FcRn |
| BMS | 2.0 | 1.7 |
| APE1922 | 2.7 | 2.9 |
| APE1923 | 4.0 | 5.0 |
| APE1924 | 3.6 | 4.0 |
| APE1950 | 34.0 | 36.5 |
| APE1963 | 9.0 | 11.9 |
| APE2058 | 2.1 | 2.0 |

The results of this example demonstrate a method of generating the inventive immunoglobulin heavy and light chain polypeptides, which exhibit thermostability and high affinity for PD-1.

Example 4

This example demonstrates the activity of the inventive immunoglobulin heavy and light chain polypeptides in vitro.

Functional antagonist activity of the $V_H$ and $V_L$ sequences described in Example 3 was tested in a human CD4$^+$ T-cell MLR assay as described above. For determination of functional potency, the $EC_{50}$ for each antibody was determined in five separate experiments using different human donors. The results are shown in Table 3 and demonstrate potent activity for each of the selected antibodies, which was indistinguishable from the activity of the reference antibody.

TABLE 3

| $EC_{50}$ Values (µg/mL) | | | | | | |
|---|---|---|---|---|---|---|
| BMS Reference | APE2058 | APE1922 | APE1923 | APE1924 | APE1950 | APE1963 |
| 0.01 | 0.01 | 0.01 | 0.01 | 0.01 | 0.01 | 0.01 |
| *0.03* | *0.10* | *0.10* | *0.2* | *0.03* | *0.20* | *0.10* |
| 0.02 | 0.04 | 0.03 | 0.01 | 0.04 | 0.02 | 0.02 |
| 0.01 | 0.01 | 0.01 | 0.02 | 0.01 | 0.01 | 0.07 |
| 0.01 | 0.01 | 0.01 | 0.01 | 0.01 | 0.01 | 0.01 |

Each line represents an independent experiment using different human donors for the responder CD4$^+$ T cells.
Italicized line with one responder produced higher IL-2 levels in the presence of the affinity-matured mAbs than in the other experiments, artificially raising the $EC_{50}$ values.

The results of this example demonstrate that the inventive immunoglobulin heavy and light chain polypeptides can antagonize PD-1 signaling, resulting in increased T-cell activation.

Example 5

This example demonstrates that a combination of the inventive PD-1 binding agent and either an anti-LAG-3 antibody or an anti-TIM-3 antibody enhances T-cell activation in vitro.

To establish parameters for combination studies, the anti-PD-1 antibody APE2058 was titrated in a dose response in the human CD4+ T-cell MLR assay described above. Antagonism of PD-1 signaling resulted in increased T-cell activation and a corresponding 4- to 5-fold increase in the production of IL-2.

Based on the results from titrating the APE2058 antibody in multiple MLR assays, an $EC_{50}$ value of 20 ng/mL and a concentration 10-fold lower that represents an approximate $EC_{10}$ value (2 ng/mL) were selected for combination studies with antagonist antibodies to the TIM-3 or LAG-3 checkpoint molecules.

Figure 2:
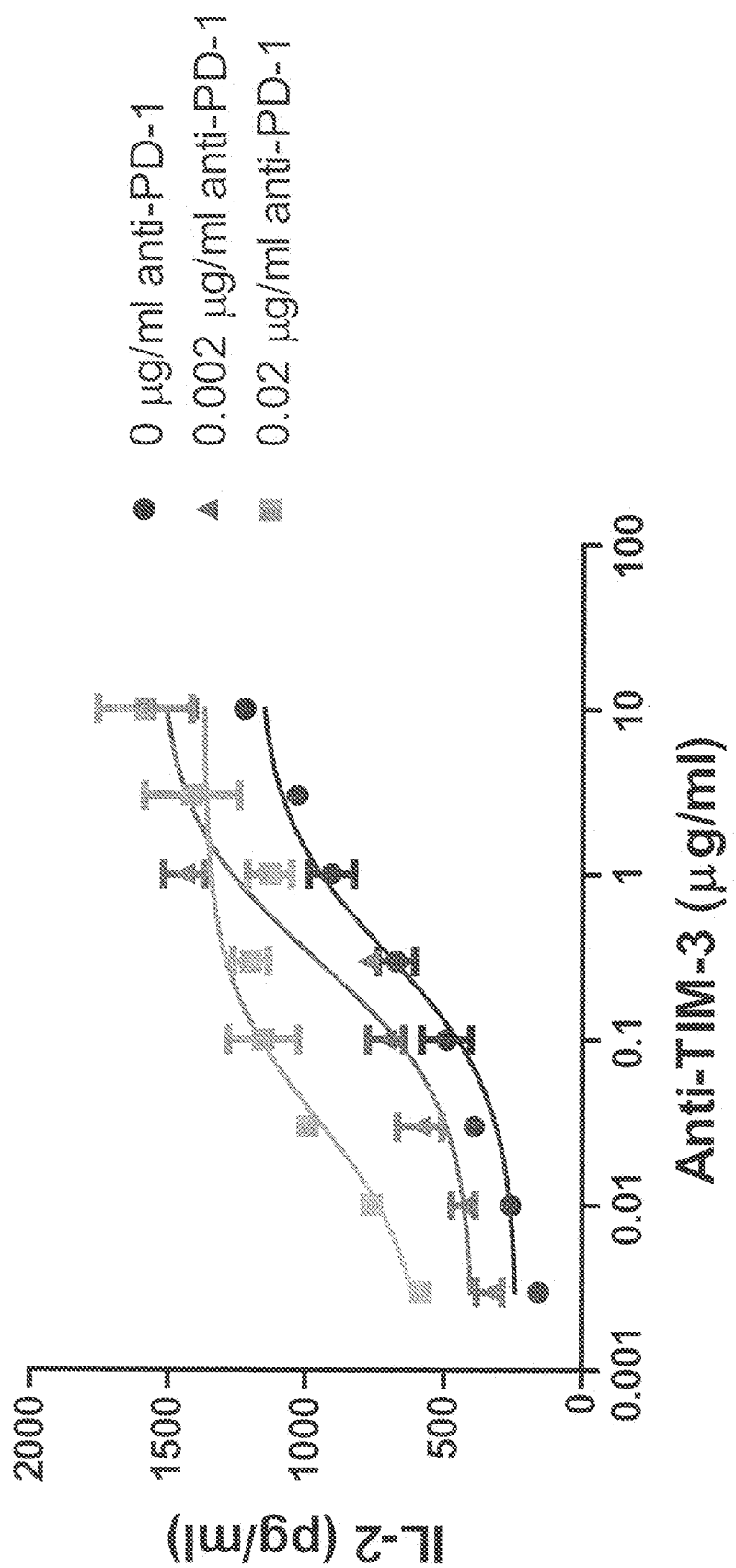
FIG. 2 is a graph which illustrates experimental results demonstrating increased activity of an anti-TIM-3 antagonist antibody in a human CD4+ T-cell MLR assay in the presence of low levels of anti-PD-1 antibody APE2058.

A fully human anti-TIM-3 antibody was characterized in a CD4+ T cell in vitro assay as having antagonist activity as measured by increased IL-2 production in the presence of low levels of anti-CD3 and anti-CD28 antibodies. The anti-TIM-3 antibody demonstrated activity in the MLR assay with an $EC_{50}$ value of approximately 0.3 µg/mL, as shown in FIG. 2 and Table 4, which is approximately 15-fold less activity than the anti-PD-1 APE2058 antibody alone ($EC_{50}$ approximately 0.02 µg/mL). In combination with 0.02 µg/mL of APE2058, the anti-TIM-3 antagonist antibody stimulated increased amounts of IL-2 production as compared to APE2058 or anti-TIM-3 alone, resulting in a 10-fold decrease in the $EC_{50}$ values, as shown in FIG. 2 and Table 4. These results demonstrate that enhanced T-cell activation occurs with combination inhibition of the PD-1 and TIM-3 checkpoint pathways.

Figure 3:
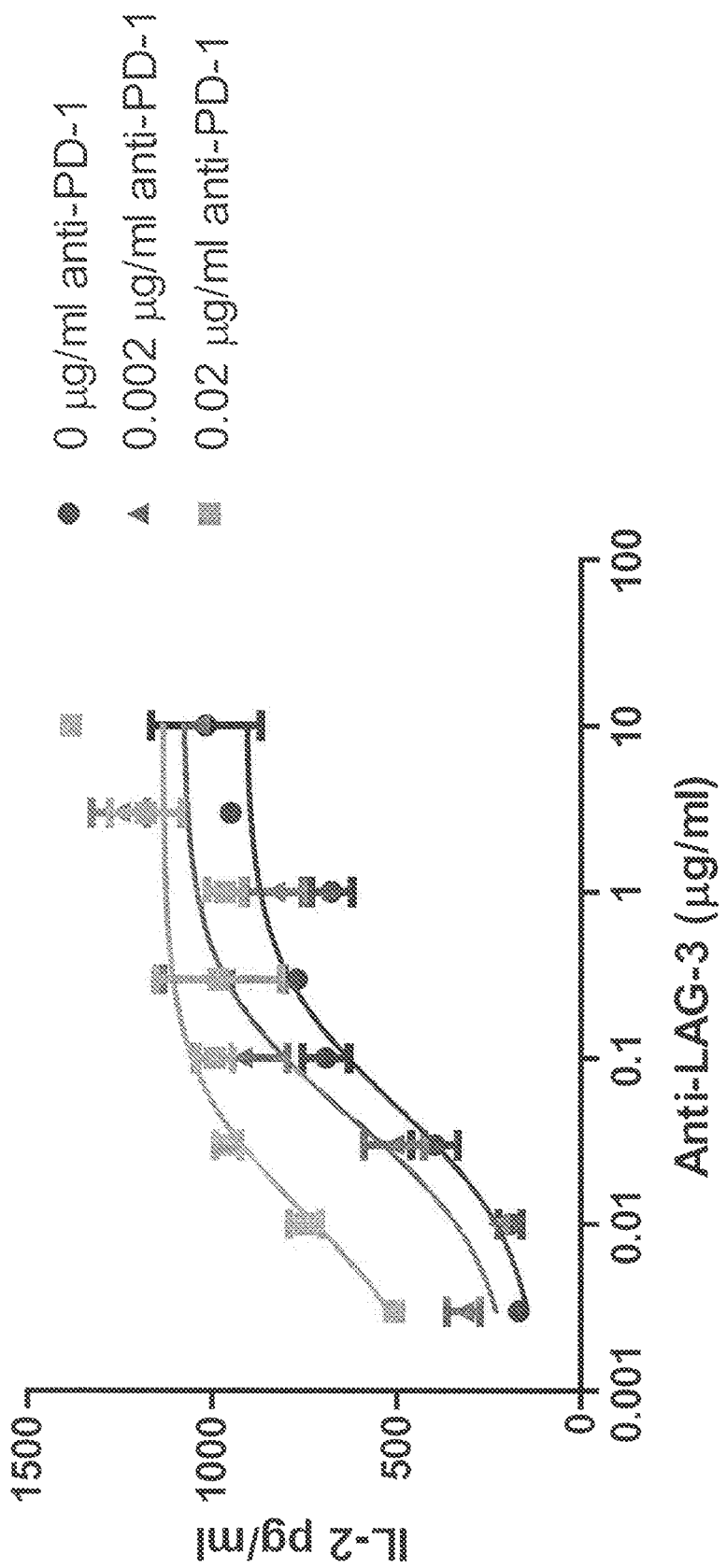
FIG. 3 is a graph which illustrates experimental results demonstrating increased activity of an anti-LAG-3 antagonist antibody in a human CD4+ T-cell MLR assay in the presence of low levels of anti-PD-1 APE2058.

A fully human antagonist anti-LAG-3 antibody (described in U.S. Patent Application Publication 2011/0150892) has demonstrated potent activity in blocking binding of recombinant soluble LAG-3 to MHC Class II positive cells. This antibody, designated herein as APE03109, was evaluated for functional activity in the human CD4$^+$ T-cell MLR assay. APE03109 demonstrated activity in the MLR with an $EC_{50}$ value of approximately 0.05 µg/mL, as shown in FIG. 3 and Table 4, which was similar to the activity of the anti-PD-1 antibody alone. In combination with 0.02 µg/mL of the anti-PD-1 APE2058 antibody, the APE03109 antibody stimulated increased amounts of IL-2 production over APE2058 or APE03109 alone, resulting in a 5-fold decrease in the $EC_{50}$ values.

A time course of IL-2 production with the anti-LAG-3 APE03109 antibody alone and the combination of APE2058 with APE03109 also was characterized in a human CD4$^+$ MLR assay. A similar decrease in $EC_{50}$ value for the combination of 0.02 µg/mL APE2058 and APE03109 was observed after 72 hours of culture, as shown in FIG. 3. After 96 hours of culture the differences in $EC_{50}$ values were not as pronounced; however, the levels of IL-2 produced in the cultures treated with 0.02 µg/mL of the anti-PD-1 APE2058 antibody and the anti-LAG-3 APE03109 antibody almost doubled as compared to cultures treated with APE03109 alone (2,200 pg/mL versus 1,200 pg/mL). Consistent with the time course of LAG-3 expression, no increased IL-2 production from adding APE03109 to APE2058 was observed after 24 hours, although APE2058 alone produced a dose responsive increase in IL-2 production at this time. In separate MLR experiments it was also demonstrated that the combination of APE2058 and APE03109 enhanced the levels of production of the T-cell cytokine IFN-γ by over 50% after 48 hours.

To demonstrate that the combined effects of the anti-TIM-3 antibody or the anti-LAG-3 antibody in the CD4$^+$ T-cell MLR were due to target specificity, an irrelevant human IgG1 antibody, APE0422, was tested in combination with 0.02 µg/mL anti-PD-1 antibody APE2058. At the highest concentration tested (30 µg/mL), the APE0422 antibody exhibited no effect on IL-2 production over anti-PD-1 alone.

TABLE 4

| Antibody | MLR Assay EC$_{50}$ Single agent | MLR Assay EC$_{50}$ with 2 ng/mL anti-PD-1 | MLR Assay EC$_{50}$ with 20 ng/mL anti-PD-1 | Fold Improvement |
|---|---|---|---|---|
| Anti-TIM-3 | 330 ng/mL | 310 ng/mL | 33 ng/mL | 10 |
| Anti-LAG-3 | 53 ng/mL | 44 ng/mL | 11 ng/mL | 4.8 |

The results of this example demonstrate that the inventive PD-1-binding agent combined with antagonistic antibodies directed against TIM-3 or LAG-3 enhances CD4$^+$ T-cell activation in vitro.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A PD-1 binding antibody comprising:
   (i) a heavy chain comprising SEQ ID NO: 23; and,
   (ii) a light chain comprising SEQ ID NO: 40.

2. The PD-1 binding antibody of claim 1 further comprising an IgG1, IgG2, or IgG4 heavy chain constant region.

3. A method of treating cancer in a human comprising administering an effective amount of the antibody of claim 1.

4. A method of treating cancer in a human comprising administering a PD-1 binding antibody comprising (i) a heavy chain comprising SEQ ID NO: 23; and, (ii) a light chain comprising SEQ ID NO: 40; wherein the cancer is melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma.

5. The method of claim 4, further comprising administering an effective amount of a TIM-3 binding antibody.

6. A method of treating lung cancer in a human comprising administering a PD-1 binding antibody comprising (i) a heavy chain comprising SEQ ID NO: 23; and, (ii) a light chain comprising SEQ ID NO: 40.

7. The method of claim 6, further comprising administering an effective amount of a TIM-3 binding antibody.

8. A pharmaceutical composition comprising the PD-1 binding antibody of claim 1 and a pharmaceutically acceptable carrier or diluent.

9. The method of claim 3, further comprising administering an effective amount of a TIM-3 binding antibody.

* * * * *

UNITED STATES PATENT AND TRADEMARK OFFICE
CERTIFICATE OF CORRECTION

PATENT NO. : 10,738,117 B2
APPLICATION NO. : 15/726287
DATED : August 11, 2020
INVENTOR(S) : David J. King and Marilyn Kehry Page 1 of 1

It is certified that error appears in the above-identified patent and that said Letters Patent is hereby corrected as shown below:

On the Title Page

Item (62), Column 1 (Related U.S. Application Data), Line 1, Delete "Division" and insert -- Continuation --, therefor.

Signed and Sealed this
Thirteenth Day of October, 2020

Andrei Iancu
*Director of the United States Patent and Trademark Office*